(12) United States Patent
Varani et al.

(10) Patent No.: US 6,630,516 B2
(45) Date of Patent: Oct. 7, 2003

(54) METHODS AND COMPOSITIONS FOR PREVENTING AND TREATING CHRONOLOGICAL AGING IN HUMAN SKIN

(75) Inventors: James Varani, Ann Arbor, MI (US); Gary J. Fisher, Ann Arbor, MI (US); John J. Voorhees, Ann Arbor, MI (US); Sewon Kang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/028,435

(22) Filed: Feb. 24, 1998

(65) Prior Publication Data

US 2001/0053347 A1 Dec. 20, 2001

Related U.S. Application Data

(60) Provisional application No. 60/040,594, filed on Feb. 25, 1997, and provisional application No. 60/042,976, filed on Apr. 7, 1997.

(51) Int. Cl.[7] ............... A61K 31/07; A61K 7/42; A61K 7/44
(52) U.S. Cl. ............... 514/725; 514/167; 514/576; 514/629; 424/59; 424/60
(58) Field of Search ............... 424/59, 60; 514/167, 514/576, 629, 725

(56) References Cited

U.S. PATENT DOCUMENTS

| 4,603,146 A | | 7/1986 | Kligman |
| 4,888,342 A | | 12/1989 | Kligman et al. |
| 5,091,171 A | * | 2/1992 | Yu et al. ............... 424/642 |
| 5,747,538 A | | 5/1998 | Meybeck et al. |
| 5,837,224 A | * | 11/1998 | Voorhees et al. ............... 424/59 |

FOREIGN PATENT DOCUMENTS

| EP | 0 391 033 A2 | 4/1989 |
| EP | 0 379 367 A2 | 7/1990 |
| EP | 0 486 395 A1 | 5/1992 |
| WO | WO 95/25524 A1 | 9/1995 |
| WO | WO 97/2569 A1 | 7/1997 |
| WO | WO 98/55075 A2 | 12/1998 |

OTHER PUBLICATIONS

Gary J. Fisher, "Molecular Basis of Sun–Induced Premature Skin Aging and Retinoid Antagonism", Nature, Jan. 25, 1996, vol. 379 pp. 335–339, USA.
EPO Search Report, Apr. 20, 2000.
British J. of Dermatology, Dec. 1996, vol. 135 No. 6, pp. 867–875, Gilchrest, et al.
British J. of Dermatology, Jun. 1995, vol. 132 No. 6, pp. 841–852, Gniadecki, et al.

\* cited by examiner

*Primary Examiner*—Shelley A. Dodson
(74) *Attorney, Agent, or Firm*—Bradley N Ruben, PC

(57) ABSTRACT

The deleterious effects of the passage of time on human skin (i.e., chronological aging of human skin) can be prevented and treated with the topical application of a retinoid, preferably retinol. We have found that some of the same pathways (namely the stress-activated pathways, SAPs) activated in photoaging of human skin (i.e., sun-induced premature skin aging) are similarly elevated in the skin of elderly people. We have also found that other pathways (namely the mitogen-activated ERK pathway) is depressed in the same skin. Treatment of chronologically-aged skin with a non-retinoid MMP inhibitor and optionally a retinoid both inhibits degradation of dermal collagen and promotes procollagen synthesis. Biopsied sections from skin of elderly (80+ years old) show that a single treatment can increase epidermal thickness, improve the dermal collagen density, and promote the formation of rete pegs and dermal papillae (see FIG. 13), and can decrease the amount of c-Jun and increase the amounts of Types I and III procollagen (see FIG. 18). Such benefits are also helpful in preventing bruising, tearing, and ulceration of elderly skin.

38 Claims, 18 Drawing Sheets

(2 of 18 Drawing Sheet(s) Filed in Color)

FIGURE 3
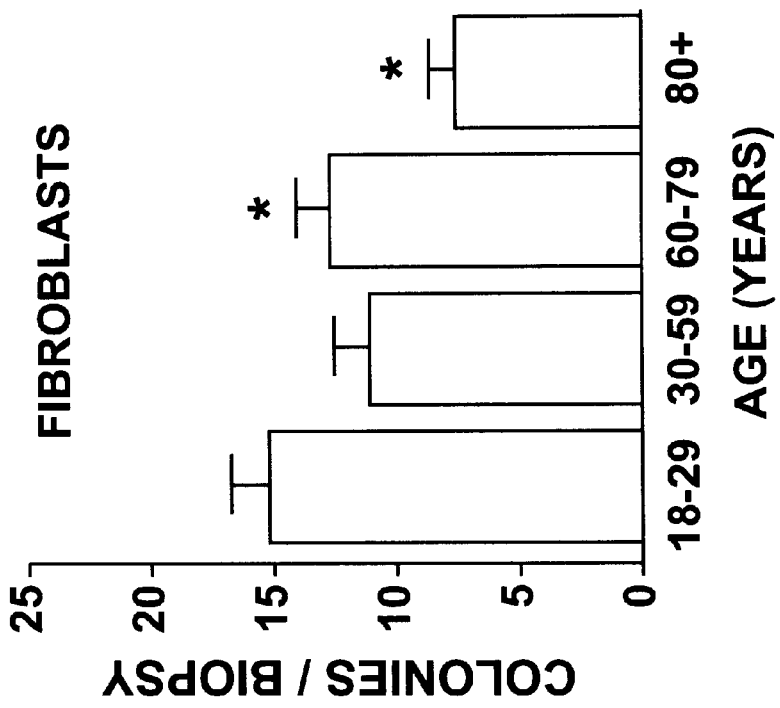
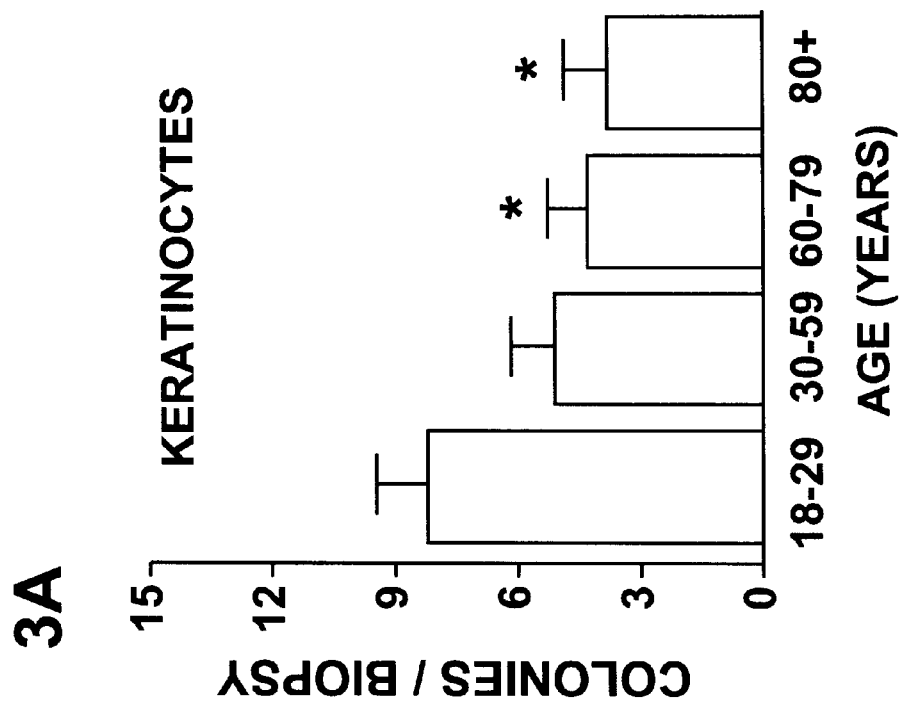

FIGURE 18
18A
c-Jun
VEH ROL
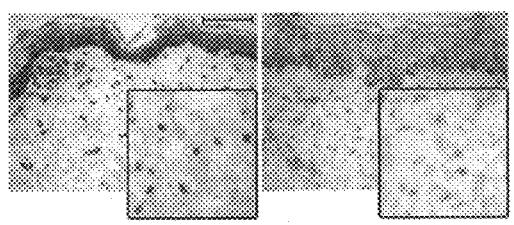
18B
Type I Procollagen
VEH ROL
18C
Type III Procollagen
VEH ROL
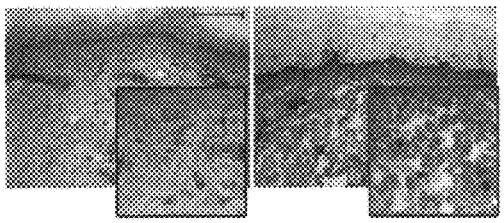

METHODS AND COMPOSITIONS FOR PREVENTING AND TREATING CHRONOLOGICAL AGING IN HUMAN SKIN

RELATED APPLICATIONS

This application is based in part on provisional applications Nos. 60/040,594, filed Feb. 25, 1997, and 60/042,976, filed Apr. 7, 1997, the disclosures of which are incorporated herein by reference.

BACKGROUND OF THE INVENTION

1. Field of the Invention

This invention relates to methods and compositions, especially those comprising retinoids, preferably topically applied, which are useful for improving keratinocyte and fibroblast proliferation, decreasing matrix metalloproteinase (MMP) expression, and improving collagen synthesis in elderly skin, thus providing as an effect the rejuvenation of aged skin.

2. The State of the Art

As far as mammals go, humans are essentially hairless; that is, most of the skin of the human body can be seen without interference from hair. The skin is thus exposed to whatever insults (natural and man-made) the environment harbors. Since it was first understood that the sun caused erythema, people have taken measures to avoid its "harmful rays." A century ago, in Elizabethan England, it was the fashion to avoid the sun at all costs. Yet the skin of those Elizabethans still wrinkled and displayed other signs of chronological aging.

Human skin is a complex organ which extends over the entire body. There are different types of skin at different portions of the body; for example, facial skin is different from that of the scalp, and even the skin on the front (palm) of the hand is different than that on the back of the hand. Although the type of skin can vary over a person's body, skin is generally composed of two main layers of tissue. The epidermis or cuticle, the outermost layer, is composed of superficial layers (from the outside in: stratum corneum, stratum lucidem, and stratum granulosum) and deep layers (stratum spinosum and stratum basale). The dermis, cutis vera, or the true skin, is composed of a papillary layer above and a reticular layer below.

Since ancient times, a variety of substances have been applied to the skin to improve its appearance, generally by affecting the outermost layer of the skin, or to treat a skin ailment, generally by affecting the true skin. More recently, efforts have been made to rejuvenate the skin and reclaim the elasticity and suppleness lost from exposure to sunlight (UV radiation) and weather.

There is a difference between the physiology of chronologically-aged or intrinsically-aged skin (old skin) in comparison with that of photoaged skin (i.e., skin that appears old due to damage from solar UV irradiation). Old skin typically maintains a smooth and unblemished appearance, in comparison with the leathery, blotchy, and often deep wrinkling of photoaged skin. The epidermis of old skin is typically thinner than normal, whereas that of photoaged aged skin is typically thicker than normal (acanthotic) and atrophies over time. Photoaged skin typically has a large Grenz zone (a wide band of eosinophilic material just beneath the epidermis, and collagen formation and structures indicative of wound healing) which is absent from chronologically-aged skin. See also N. A. Fenske and C. W. Lober, "Structural and functional changes of normal aging skin," *J. Am. Acad. Dermatol.,* 15:571–585 (1986).

Kligman et al., in EP-A2-0 379,367 describe a method for the treatment or prevention of intrinsically aged skin with retinoids. Kligman et al. tested all trans-retinoic acid (as Retin-A® cream) on albino hairless mice and on 5 elderly Caucasian women; only clinical observations were made of the women before and after the study, and only one biopsy was reported taken and this occurred six months into the treatment (i.e., there is no disclosure in this publication of a reference biopsy taken from the biopsied subject before treatment or from an early period of treatment).

U.S. Pat. Nos. 3,932,665 and 4,934,114 disclose the use of retinal (Vitamin A aldehyde), for the treatment of acne and for the treatment of skin keratoses, respectively; see also U.S. Pat. No. 3,060,229. Retinal and it derivatives have also been suggested as useful in the treatment of such conditions as wrinkles, warts, psoriasis, eczema, dandruff, and the like (see EP-A2-0 391 033). There is also evidence to indicate that tretinoin (all trans retinoic acid) improves the appearance of photoaged skin. Albert M. Kligman, "Current Status of Topical Tretinoin in the Treatment of Photoaged Skin," *Drugs & Aging,* 2 (1):7–13 (1992); and Chas. N. Ellis et al., "Tretinoin: Its Use in Repair of Photodamage," and A. S. Zelickson et al., "Topical Tretinoin in Photoaging: An Ultrastructural Study," both in *Journal of Cutaneous Aging & Cosmetic Dermatology,* Vol. 1, No. 1, p. 33–40 and 41–47 (1988).

Burger et al., in U.S. Pat. No. 5,665,367, describes compositions for topical application to the skin that contain naringenin and/or quercetin, and a retinoid. The compositions are described as useful for treating many unrelated skin conditions, such as wrinkles, acne, skin lightening, and age spots. The action of their composition on human skin is described with respect to an enzyme (transglutaminase) important to the formation of the cell envelope and thus to the epidermis. In contrast, the present invention is directed to changes in the dermis and the proliferation of beneficial dermal cells and structures.

SUMMARY OF THE INVENTION

The primary invention is the discovery of a method for rejuvenating human skin. As used with respect to the description and claiming of this invention, "rejuvenating" includes the steps of simultaneously preventing collagen degradation and stimulating the formation of new collagen in aged human skin. The invention is based on biopsies of treated and untreated sun-protected human skin from aged (80+ year old) volunteers compared with biopsies of sun-protected skin from younger individuals. In comparison with the skin from younger people, aged skin is thinner, has fewer cells in the epidermis (keratinocytes) and dermis (fibroblasts), has less dense and more disorganized connective tissue, has higher levels of cJun kinase activity and matrix metalloproteinases (MMPs), and has reduced levels of ERK activity, cyclin $D_2$, and Types I and III procollagen.

In summary, we have found as one invention that aged human skin can be rejuvenated by the topical administration of one or more compounds in amounts effective to inhibit collagen degradation and to promote procollagen synthesis, the application preferably being performed on a regular basis. A preferred class of compounds that perform both functions are retinoids, especially retinol and all trans-retinoic acid.

Aged human skin can be benefitted by enhancing procollagen synthesis. We have found as another invention that procollagen levels can be increased in aged human skin by the preferably regular application to the skin of effective amounts of a retinoid; in preferred embodiments, the treatment also includes inhibition of collagen degradation by the use of an MMP inhibitor.

In addition to treating and/or preventing chronological aging of the skin, our discovery that effective amounts of a retinoid applied to the skin can increase procollagen synthesis provides another invention in the prevention (prophylaxis) of skin ulcers. By increasing the collagen content of the skin, the form, strength, and function of the skin is enhanced. Increased procollagen synthesis, and thus an increase in collagen content of the skin, mitigates the loss of strength and support due to reduced, degraded collagen, and so improved procollagen synthesis is expected to diminish the occurrence and/or severity of skin ulcers.

In connection with the foregoing, we have found as yet other inventions that keratinocytes and fibroblasts, each beneficial to the integrity of the skin, are each increased in number by the topical application of a retinoid, again applied preferably on a regular basis. Fibroblasts are trophic to the epidermis; under normal conditions they secrete a number of growth factors (e.g., FGF, IGF, and KGF, among others) and produce procollagen that enters the dermal matrix and become structural collagen.

Yet another invention is decreasing cJUN activity and/or reducing, the amount of c-Jun protein present in the skin, and increasing ERK activity, both in aged skin, by the topical application of an effective amount of a retinoid to the aged skin.

In additional embodiments, prophylaxis and treatment of dermal chronoaging are each enhanced by applying along with the active ingredient at least one additional compound selected from: a sunscreen for at least one of UVA1, UVA2, and UVB; an antioxidant; an MMP (matrix metalloproteinase) inhibitor; and mixtures thereof

BRIEF DESCRIPTION OF THE FIGURES

The patent or application file contains at least one drawing executed in color. Copies of this patent or patent application publication with color drawings will be provided by the Office upon request and payment of the necessary fee.

FIG. 3 depicts the depicts the relative growth potential (measured as the number of cell colonies per biopsy) of human keratinocytes (3A) and fibroblasts (3B) in various age populations we studied.

FIG. 18 is a photomicrograph showing in stained sectioned biopsies of elderly skin that, seven days after a single application of 1% retinol, c-Jun protein is decreased and the amounts of Types I and III procollagen in the skin are increased.

DESCRIPTION OF PREFERRED
EMBODIMENTS OF THE INVENTION

Figure 1:
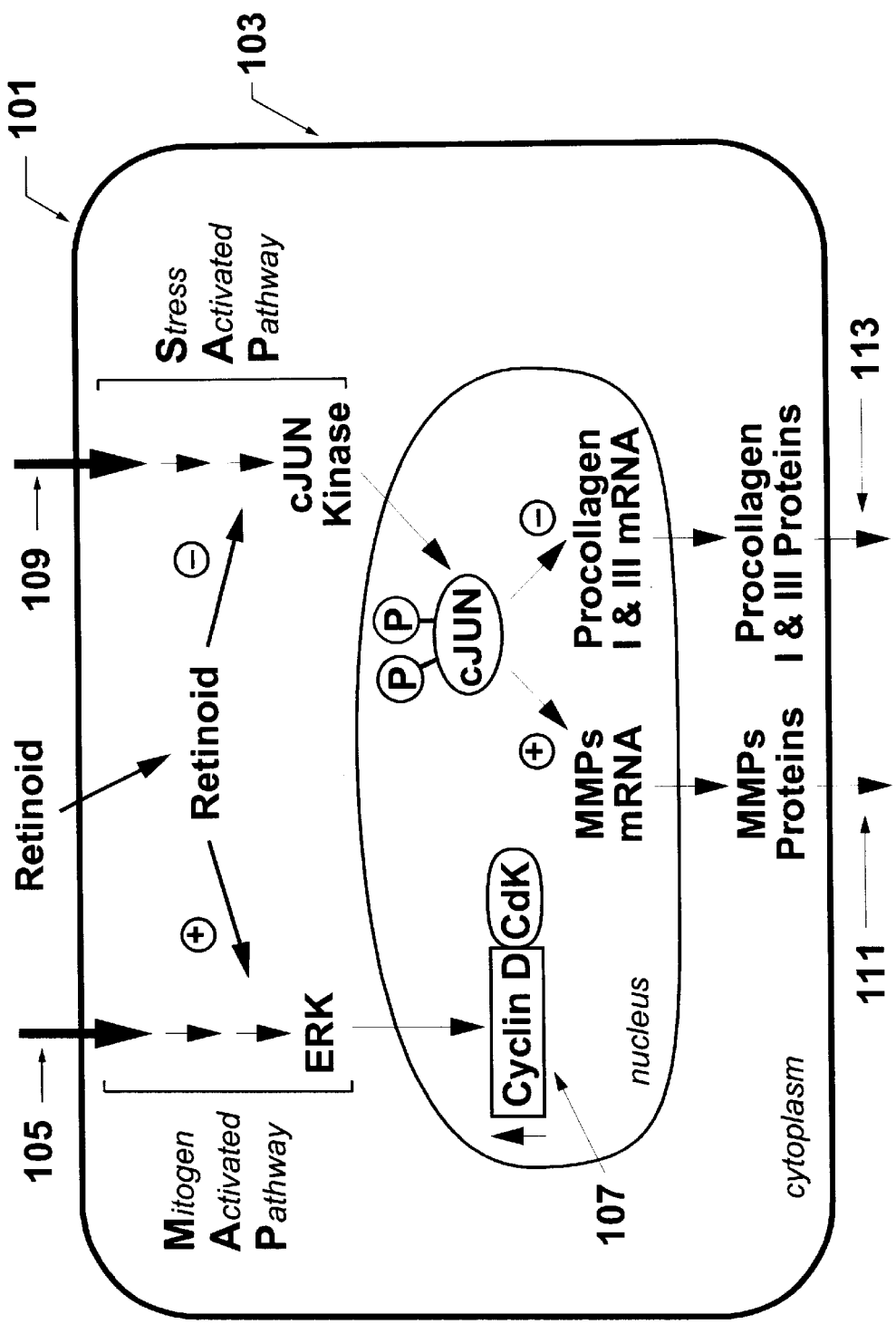
FIG. 1 depicts our representation of certain ERK and SAP pathways in an idealized skin cell.

FIG. 1 depicts certain degradative pathways that effect the functioning of an idealized skin cell based on our findings. The particularly important causes of chronological aging of human skin likely vary among a population of elderly humans, including such factors as diet, genetics, and environment. In general, though, we believe that chronological skin aging is due to activation of the stress-activated pathways (SAPs) and a repression of the mitogen-activated pathways (ERK). Contrary to conventional wisdom, in comparison with our inventions relating to photoaging of human skin, we have found that chronoaging and photoaging of human skin have a similar molecular pathophysiology. ERK mediates the actions of growth factors necessary for healthy skin. Interference with ERK can lead to thinning of chronologically-aged skin because of reduced number of cells in the epidermis and dermis. Almost conversely, SAPs activate factors (e.g., c-Jun) that promote both inhibition of procollagen synthesis and degradation of mature collagen, and thereby lead to reduced form, strength, and function of skin. Chronological aging of skin might be expected to include some interference with ERK and/or some activation of the SAPs: we have found that both events occur in chronologically-aged human skin. As shown in FIG. 1, the idealized skin cell 101 has a cell membrane 103 across which various compounds pass or at which they interact with the cell via receptors at the cell's surface. One group of inputs indicated by 105 activates the ERK pathway, which actuates ERK by phosphorylation. Activated ERK induces cyclin $D_2$ formation 107 in the cell nucleus, with the result that growth of the cell is promoted. The other group of inputs is indicated by 109, which activates the stress-activated pathway, which leads to increases in cJUN kinase activity. Once activated (again by phosphorylation), c-Jun becomes a component of AP-1, which leads to MMP formation 111 and export of MMPs from the cell, with the result being degradation of collagen in the dermal matrix. Matrix metalloproteinases (MMPs) include collagenases, gelatinases, and other enzymes naturally occurring in human skin that degrade extracellular matrix molecules, such as collagen. While not desirous of being constrained to a particular theory, we believe that increased cJUN kinase activity interferes with the synthesis of procollagen (soluble collagen precursor) which is then exported (113, with reference to FIG. 1) from the cell into the matrix to become structural collagen (insoluble collagen). We believe that activated cJUN inhibits one or more steps in the synthesis of procollagen, as shown in the figure.

Our invention is generally directed to the topical administration, preferably on a regular basis, of an amount of a retinoid, preferably retinol or retinoic acid, to the skin of an elderly person in amounts effective to induce the proliferation of at least one of keratinocytes and fibroblasts, to reduce the expression of MMPs, to stimulate the synthesis of procollagen in the elderly person's skin back to normal levels, and/or to increase the level of activated ERK and to reduce the activity of cJUN kinase and to reduce the level of c-Jun protein in elderly skin.

Analysis of Elderly Skin

Figure 2:
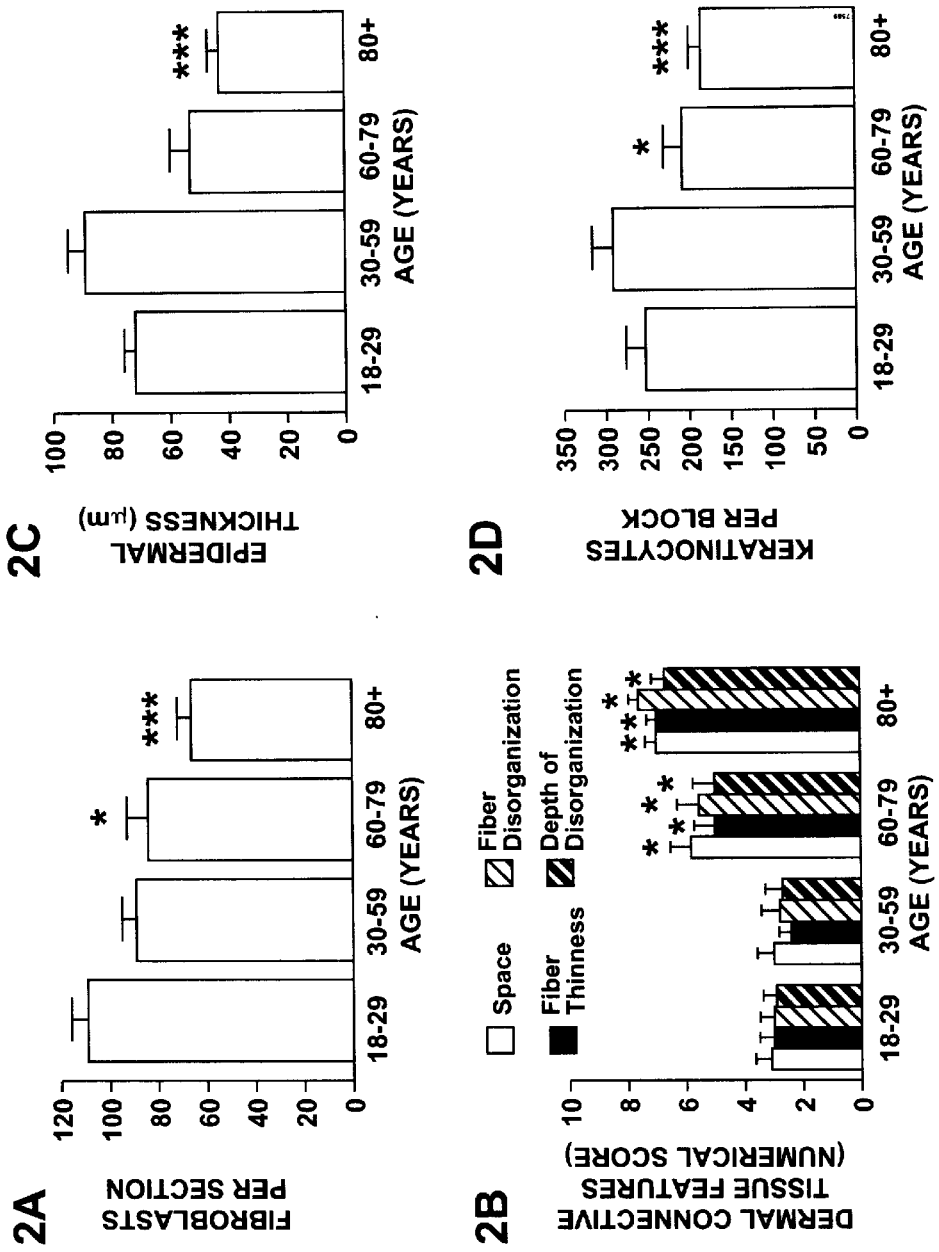
FIG. 2 depicts depicts the fibroblast density (2A), dermal connective tissue features (2B), epidermal thickness (2C), and keratinocyte density (2D) in all of the age populations we studied via biopsy.

We have found that there is an age-associated decrease in the number of keratinocytes and fibroblasts as determined from comparisons of replicate 4-mm punch biopsies obtained from the sun-protected skin of 40 individuals, ranging from 18 to over 80 years of age. Keratinocytes are the principal cell of which the epidermis is composed. The cells of the epidermis arise by differentiation of basal keratinocytes, some of which differentiate through successive overlying layers to become the stratum corneum (outermost layer of the skin). FIGS. 2A, 2B, 2C, and 2D represent morphometric data based on the entire population study we conducted. The biopsies from our volunteer population evidenced mean decreases of 27% (keratinocytes) and 39% (fibroblasts) when the youngest age group (18–29 years old) was compared with the oldest age group (80+ years old) ($p<0.1$ for both cell types), as shown in FIGS. 2A and 2D; we also note that age-associated changes in the skin are seen as a decrease in fibroblasts above age 30 and another decrease above age 80 (FIG. 2A). Our population study also evidenced an increase in the number of undesirable dermal connective tissue features above age 60 (FIG. 2B) and a decrease in epidermal thickness above age 60 (FIG. 2C). These data show there is an age-associated increase in connective tissue disorganization and/or degeneration (2.25-fold increase in oldest group compared with youngest group; $p<0.05$), as shown in FIG. 2B. The disorganization and degeneration of the connective tissues were measured by microscopic histological examination of biopsied skin tissue obtained from these elderly subjects and compared with the histology of skin biopsied from young individuals.

These findings are further confirmed by our discovery of age-associated decreases in keratinocytes (54% decrease) and fibroblasts (50% decrease) growth, determined as the number of cell colonies in culture from the biopsied tissue, compared between the same two age groups ($p<0.1$ for both cell types), as shown in FIG. 3.

Figure 4:
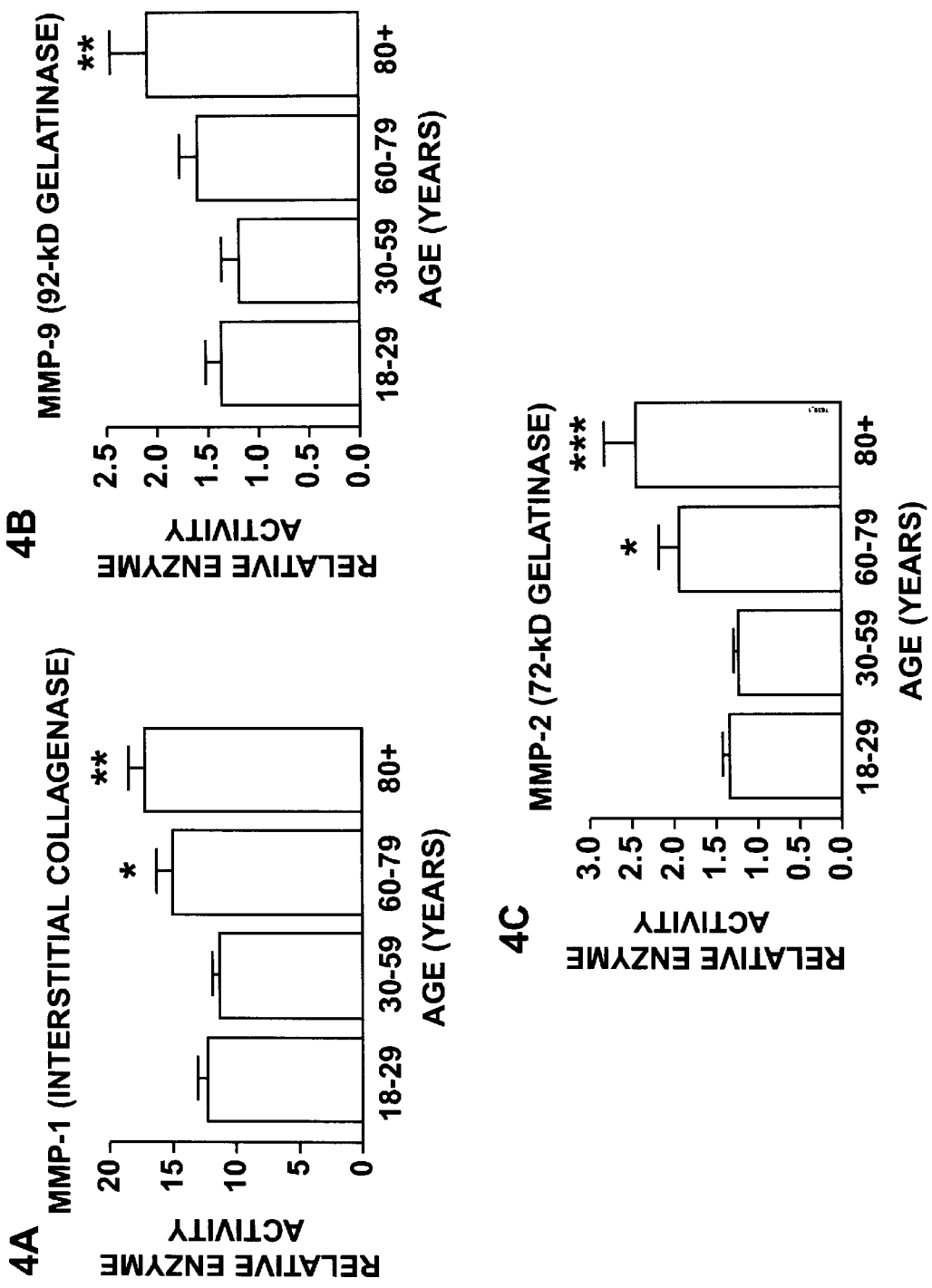
FIG. 4 depicts the relative activity of three MMPs (MMP-1 in 4A; MMP-9 in 4B, and MMP-2 in 4C) found in each of the age populations we studied.

As shown in FIG. 4, we have now also discovered an age-related increase in the relative activities of MMP-1, MMP-2, and MMP-9 when these groups of young and old individuals are compared (respectively, mean increases of 40%, 82%, and 53%, and respectively $p<0.01$, $p<0.001$, and $p<0.01$). These results were determined using replicate 4-mm punch biopsies from our 40 volunteer subjects.

Figure 5:
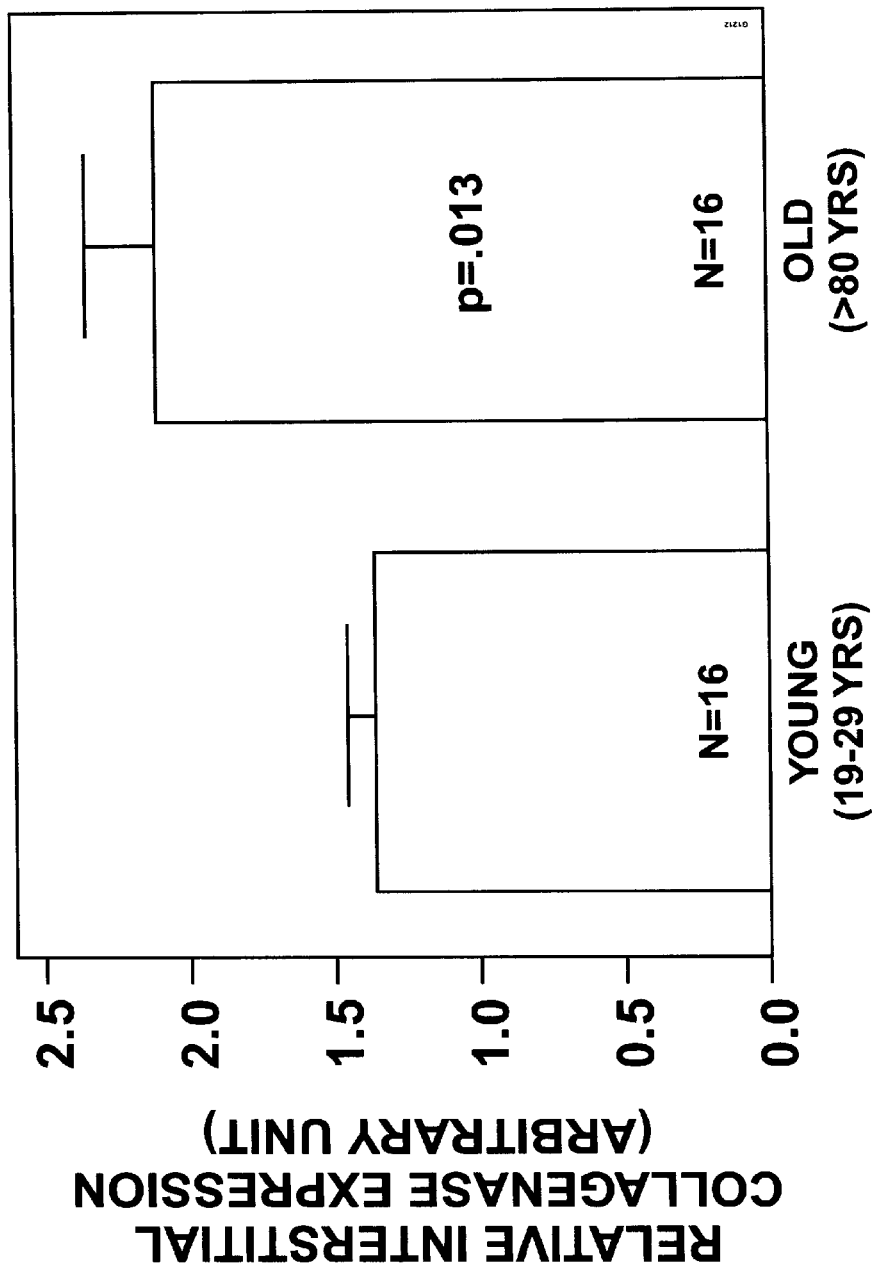
FIG. 5 depicts the differences in the expression of interstitial collagenase in vivo between young and old skin.

As shown in FIG. 5, our measurements of interstitial collagenase from the biopsied skin of 16 individuals in each of the two groups (young and old) revealed that the relative expression of the collagenase protein was present in elderly skin in amounts nearly double those found in younger subjects.

Figure 6:
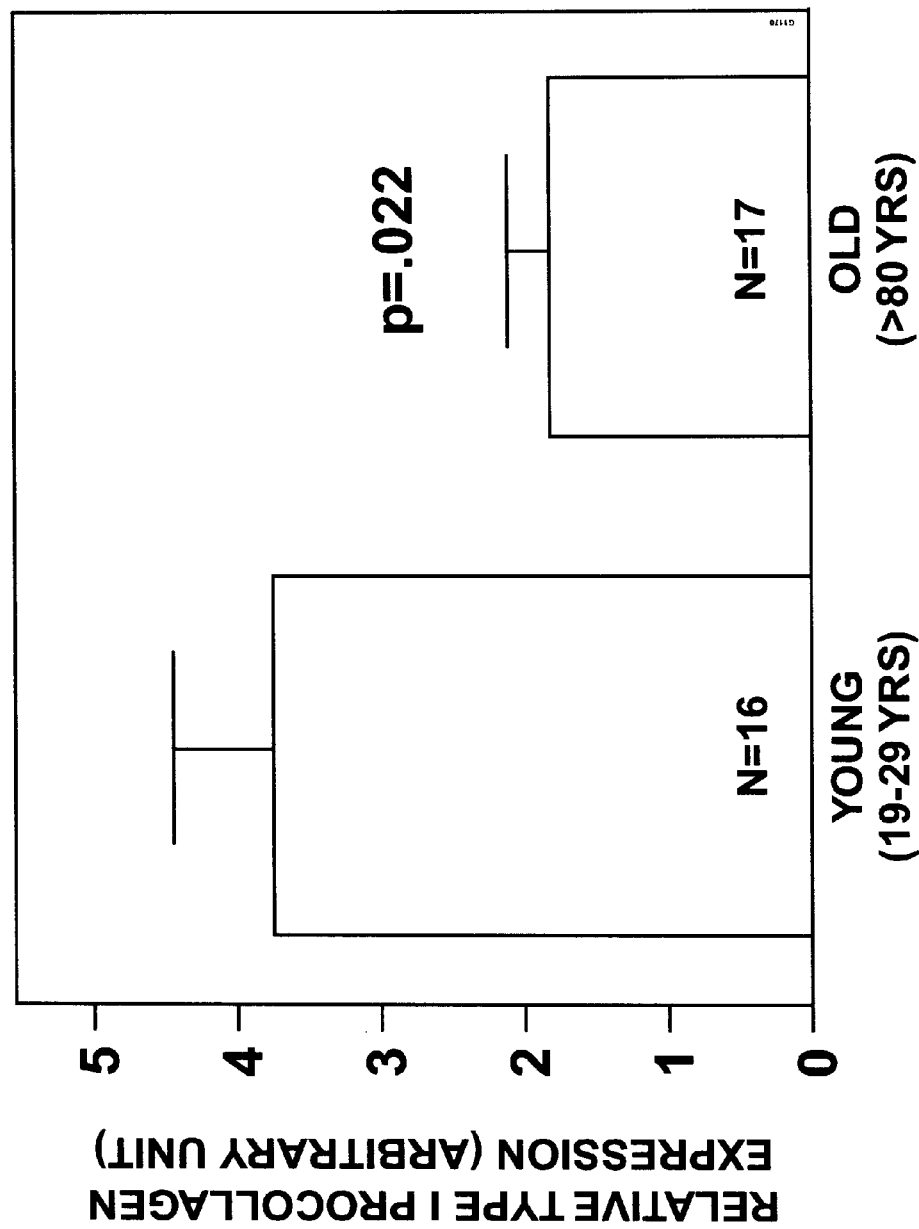
FIG. 6 depicts the differences in the expression of Type I procollagen in vivo between young and old skin.

FIG. 6 depicts our analysis to determine the presence of Type I procollagen in in vivo samples of unexposed skin taken from each of the two groups of individuals tested (young and old). We have found that about twice as much Type I procollagen is expressed in unexposed (sun-protected) young skin than in unexposed elderly skin.

Figure 7:
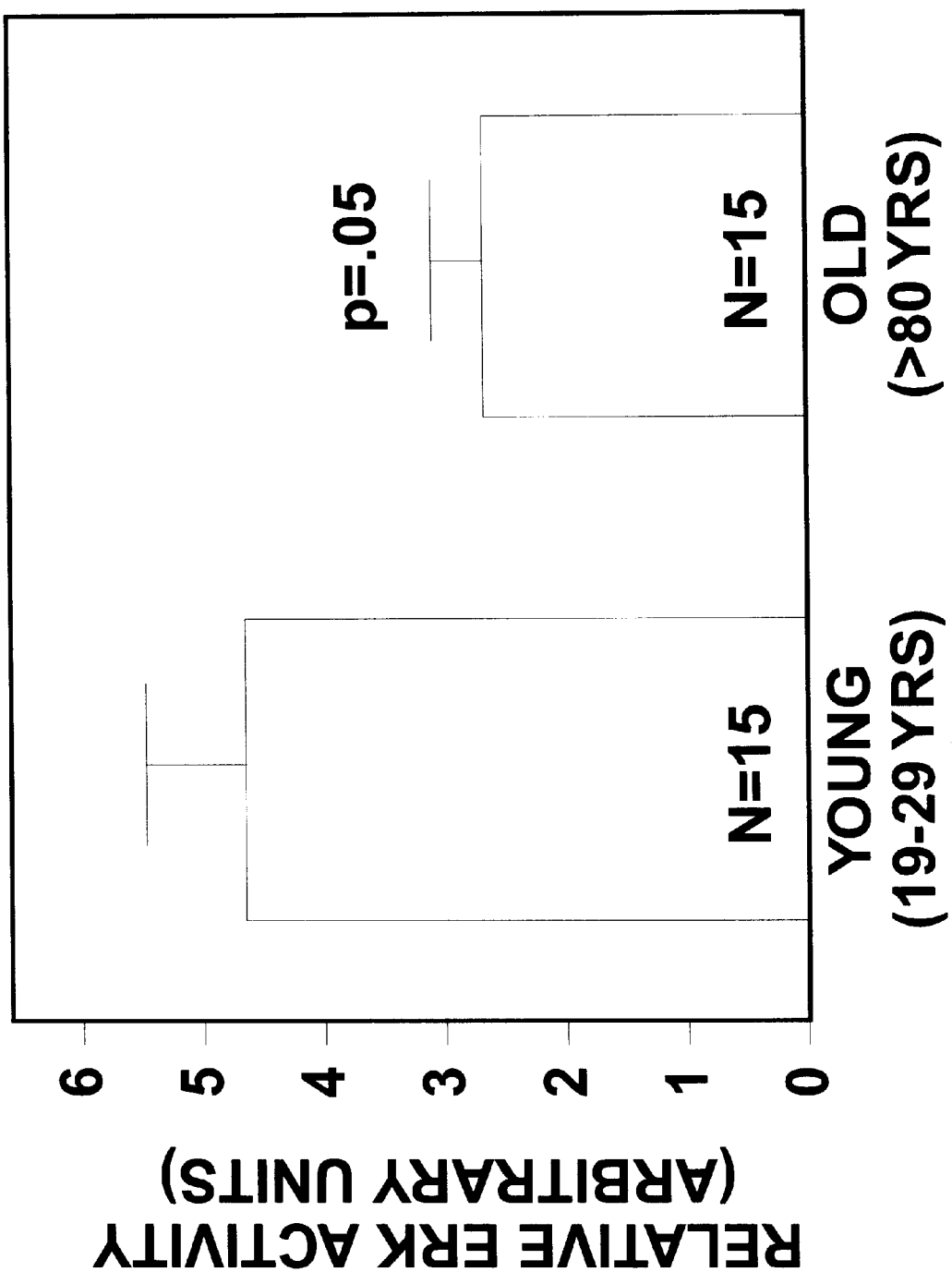
FIG. 7 depicts the differences in ERK activity in vivo between young and old skin.

FIG. 7 shows our findings for the steady state activity of ERK in skin biopsies from our volunteers, both old (over 80+ years old) and young (19–29 years old), generally according to methods as described herein. The histogram in FIG. 7 shows that the relative activity of ERK in the skin of elderly volunteers is almost half of its level of activity in the skin of younger people.

Figure 8:
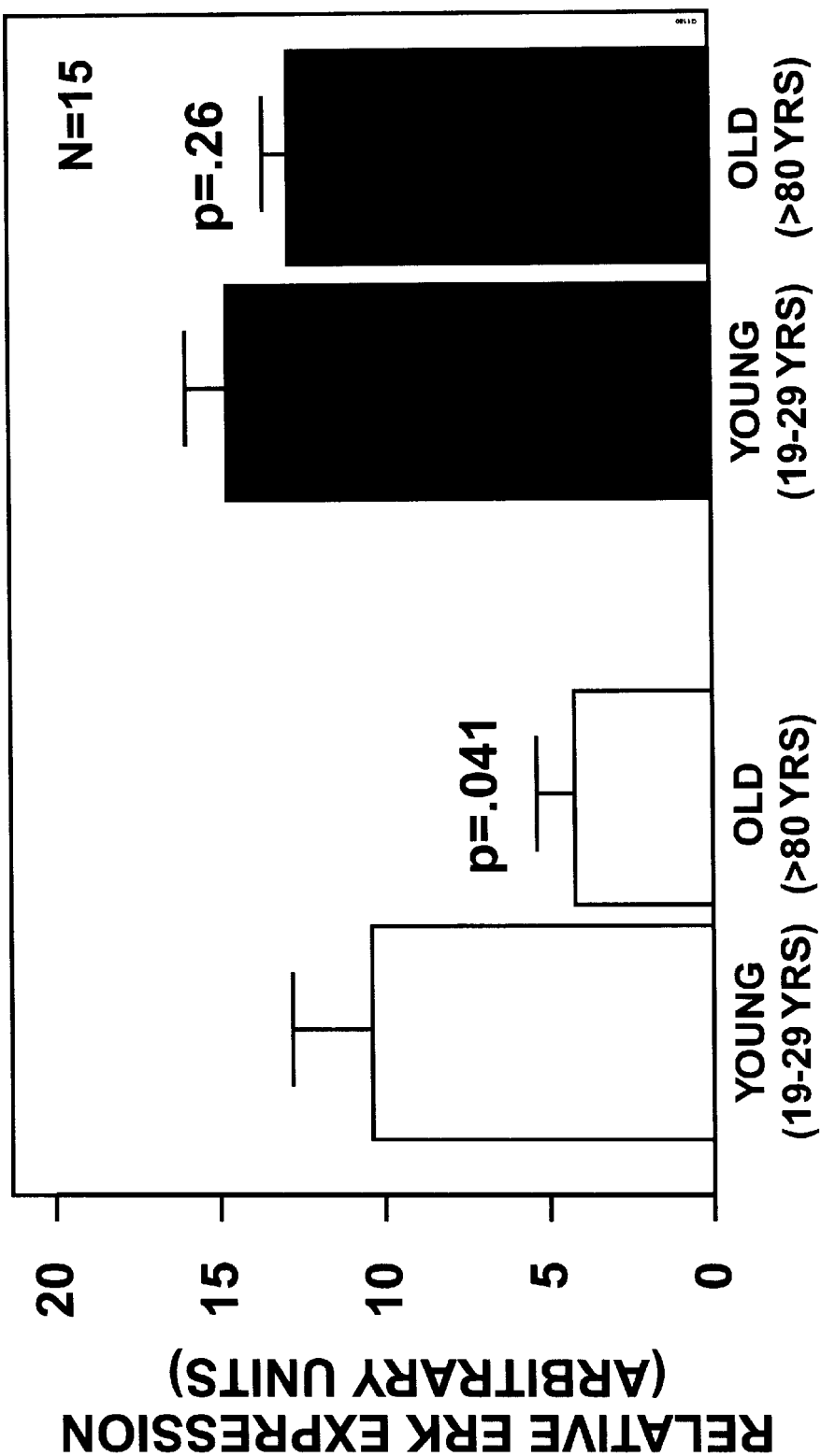
FIG. 8 depicts the differences in the expression of phosphorylated (activated) ERK in vivo between young and old skin.

Reduced ERK activity could result from reduced ERK levels or reduced ERK activation in aged skin, or from a combination of both. Therefore, we tested fifteen volunteers to determine the relative amounts of ERK present in skin, in both total and activated (phosphorylated) forms; the activated form stimulates cell growth. As shown in FIG. 8, elderly subjects had essentially the same amount of total ERK in their skin as subjects half a century younger, but had significantly less of the active, phosphorylated form of ERK. Accordingly, we have found that the reduced activity of ERK in elderly skin is not due to a reduction in the total amount of ERK, but rather to the low concentration of the activated form.

Figure 9:
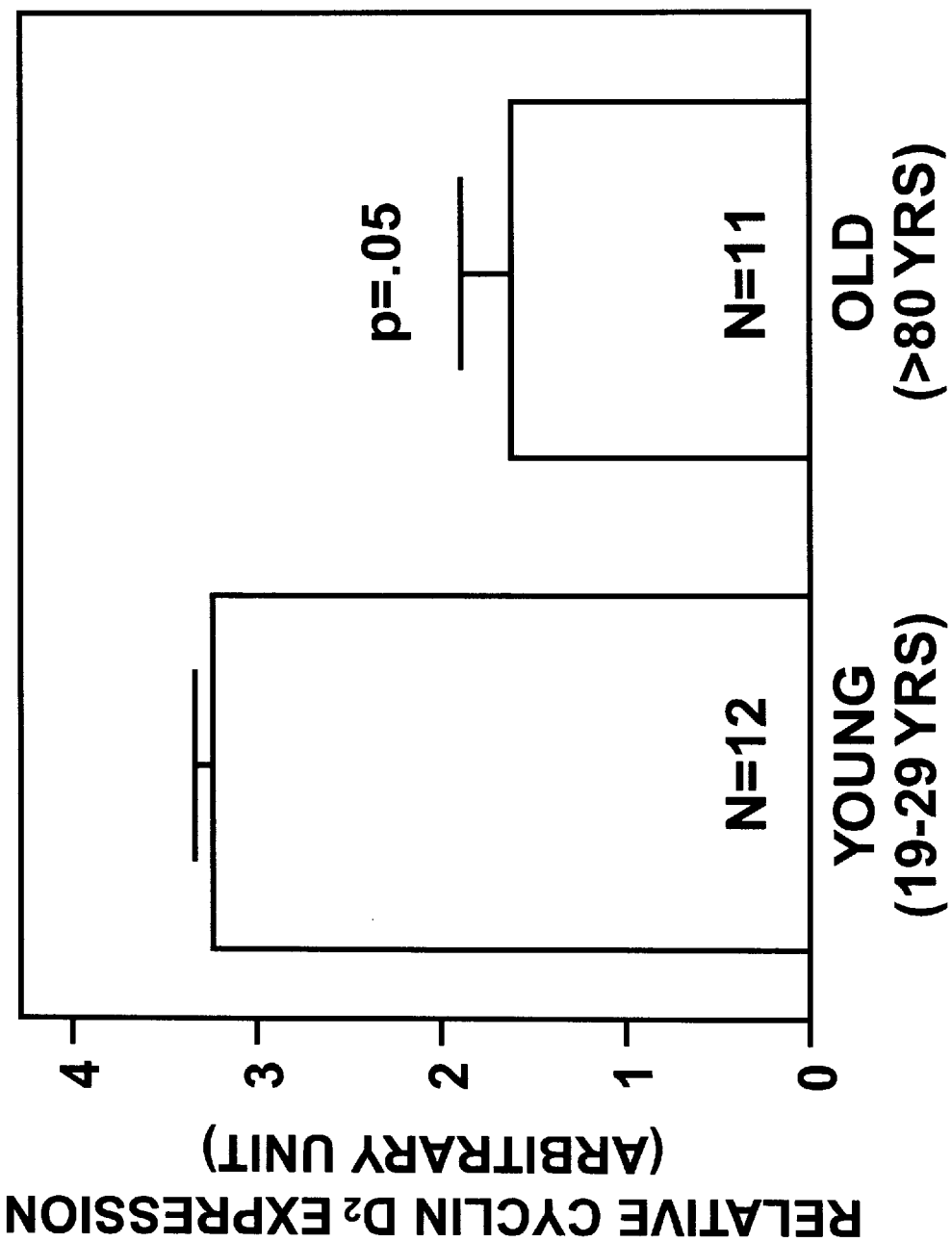
FIG. 9 depicts the differences in cyclin $D_2$ expression in vivo between young and old skin.

In the ERK pathway shown in FIG. 1, ERK induces cyclin $D_2$, which is required for cell growth. Again, interference with this ERK effector would be expected to lead to retarded cell growth and repair, and so the effects of aging on the skin would be promoted. FIG. 9 depicts our results analyzing twelve young subjects and eleven elderly subjects for expression of cyclin $D_2$ in normally covered (sun-protected) skin. The histogram of FIG. 9 shows that the amount of cyclin $D_2$ expressed in chronologically-aged skin is significantly reduced in comparison with its expression in young skin.

Figure 10:
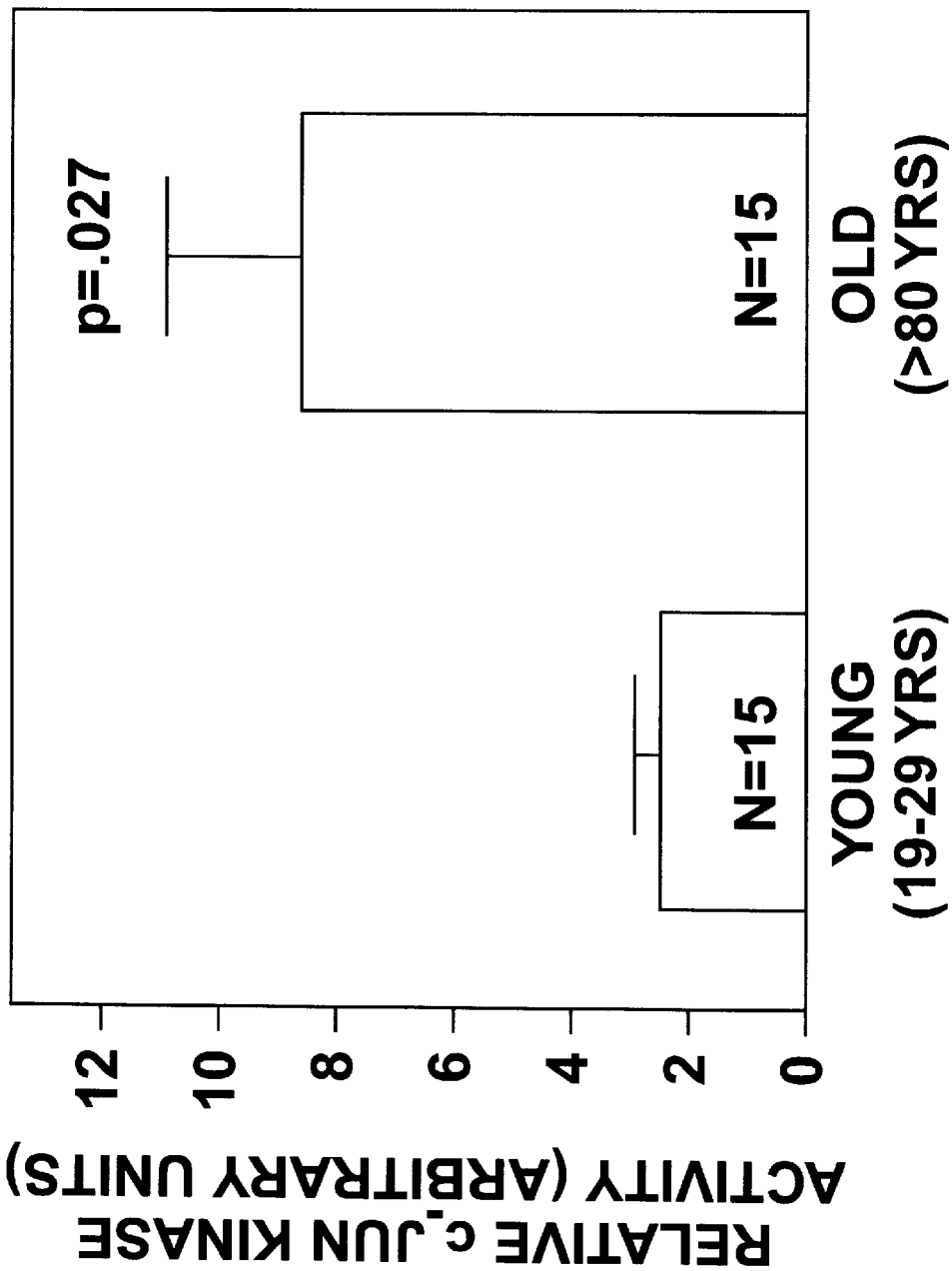
FIG. 10 depicts the differences in cJUN kinase activity in vivo between young and old skin.

We tested fifteen subjects in two age groups, young subjects (19–29) and elderly subjects (80+) to determine the degree of activation of stress-activated protein kinase ("SAPK") in each group; SAPK activity is measured by the phosphorylation of c-Jun protein. FIG. 10 shows that in vivo samples of unexposed skin from the young subjects had about 25% of the relative cJUN kinase activity than did unexposed skin from elderly subjects. From these results, one would then expect elevated levels of activated c-Jun in the skin of the elderly to lead to increased MMP activity.

Retinoid Treatment of Aged Skin

Returning again to FIG. 1, activation of SAP (stress-activated pathways 109) promotes the degradation of skin collagen through the production of MMPs including collagenase and the 92 kDa gelatinase. The SAP can be activated or up-regulated by UV radiation (as described in our copending application Ser. No. 08/588,771, filed Jan. 16, 1996, and provisional applications No. 60/048,520, filed Jun. 4, 1997, and 60/057,976, filed Sep. 5, 1997, all related to photoaging of human skin, the disclosures of which are incorporated herein by reference), tumor necrosis factors (e.g., TNF-α), interlukins (e.g., IL-1α), and other stresses. As described in the just noted '771 application and '520 and '976 provisional applications, AP-1 induces MMPs, enzymes that degrade collagen. While we have shown in the above-referenced photoaging patent applications that we can interfere with UV-induced production of collagenases, there are additional pathways involved with chronological aging, and so pathways effecting chronoaging of the skin (e.g., the ERK pathway) are not necessarily intended to be effected when a patient is treated for photoaging of the skin (for example, using a compound that only inhibits the formation of MMPs will not necessarily effect the ERK pathway).

Figure 11:
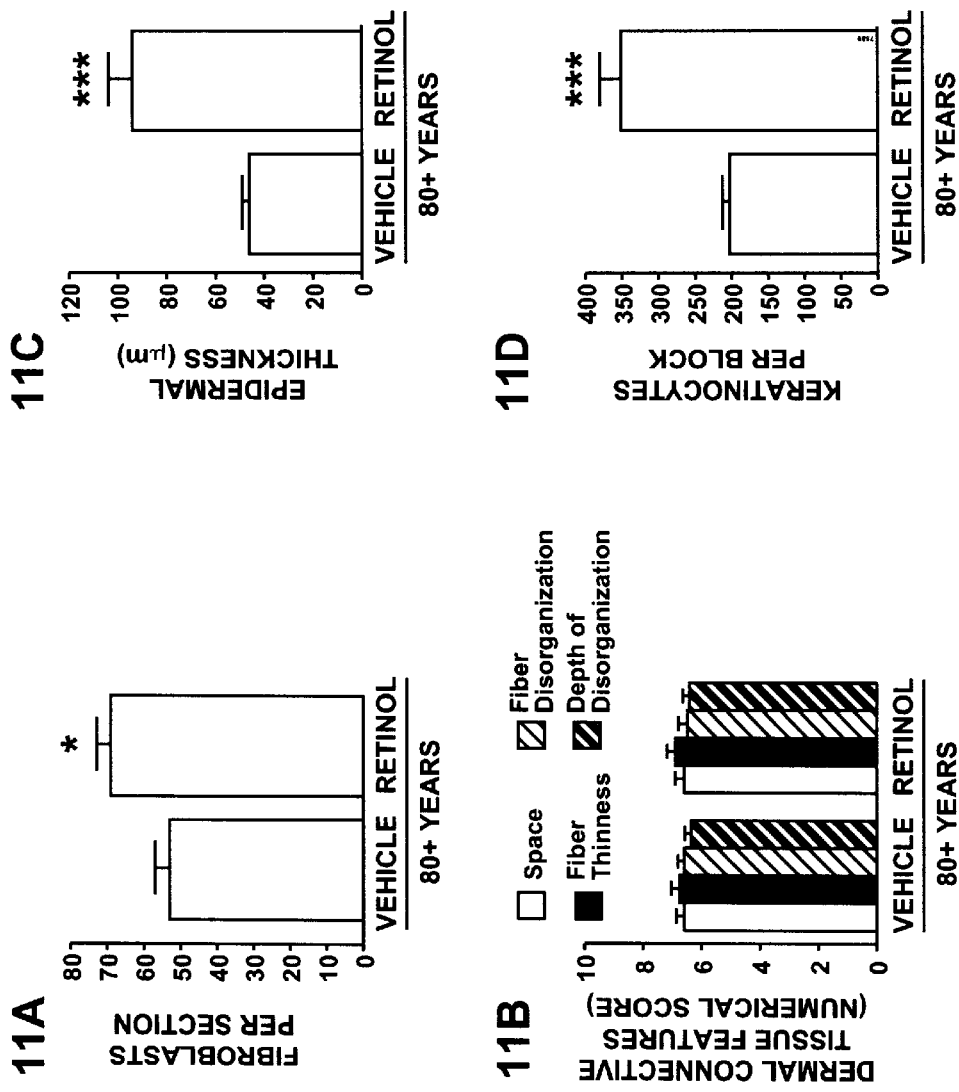
FIG. 11 depicts the change in fibroblast density (11A), dermal connective tissue features (11B), epidermal thickness (11C), and keratinocyte density (11D) in elderly (80+ years old) skin upon application of a retinoid (1% retinol; one application, occluded, and examined seven days later).

To investigate the treatment of chronologically-aged skin, 17 subjects having an age of at least 80 years old were given one topical treatment with 1% retinol or with vehicle alone, the test area was occluded for seven days, and the test area was then biopsied. The vehicle was composed of a mixture of ethanol and polyethylene glycol in a 70:30 volumetric ratio. In comparing vehicle-treated skin with untreated skin from individuals of the same elderly age range, there were no statistically significant differences in any of the parameters described with reference to FIG. 2, namely the number of fibroblasts and keratinocytes, the epidermal thickness, and undesirable dermal connective tissue features. In comparing retinol-treated skin with vehicle-treated skin from the same individuals, as shown in FIG. 11, there were increased numbers of keratinocytes (11A) and fibroblasts (11D) per section in the retinol-treated skin (273% ($p<0.001$) and 30% ($p<0.05$) mean increases, respectively). In addition, retinoid treatment increased the epidermal thickness substantially (11C). Due to the short duration of the retinoid (retinol) treatment, little change in the number of detrimental dermal connective tissue features (11B) was apparent.

Figure 12:
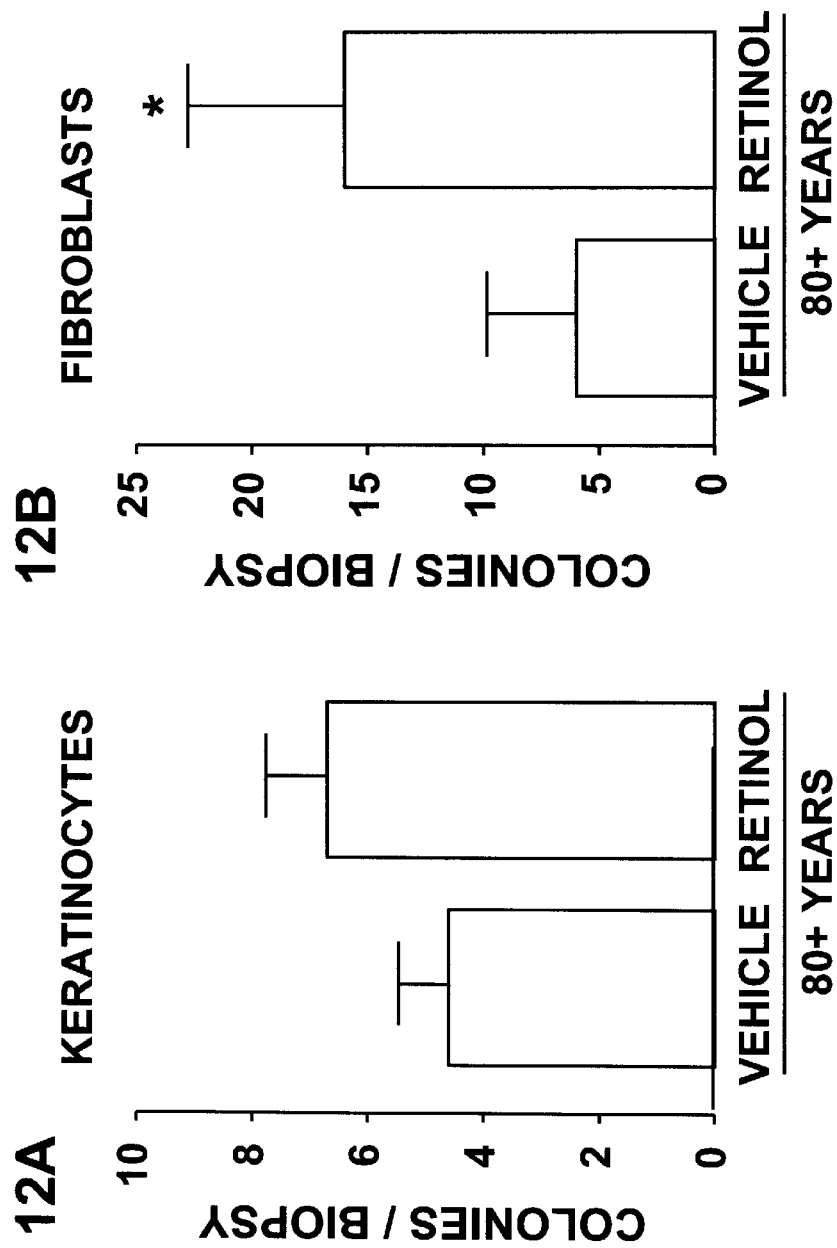
FIG. 12 depicts the effect of retinoid (retinol) treatment on the growth of human keratinocytes and fibroblasts cells cultured ex vivo from biopsy samples.

FIGS. 12A and 12B demonstrate the effects of 7-day in vivo retinol treatment on ex vivo growth of keratinocytes and fibroblasts extracted from biopsies of sun-protected skin take from our individual volunteers over age 80. That is, an elderly volunteer was treated with retinol (one application of 1% retinol, occluded for seven days), the treated area was biopsied, and the keratinocytes and fibroblasts from the biopsy were cultured ex vivo. This retinol treatment of the cells in vivo resulted in a substantial increase in the ex vivo growth of both cell types. In particular, keratinocytes growth increased by about 30% (12A) while fibroblast growth increased by about 200% (12B), with $p<0.05$ for both. Accordingly, the topical application of a retinoid to aged skin would be expected to increase the number of keratinocytes and/or the number of fibroblasts in the skin.

Figure 13:
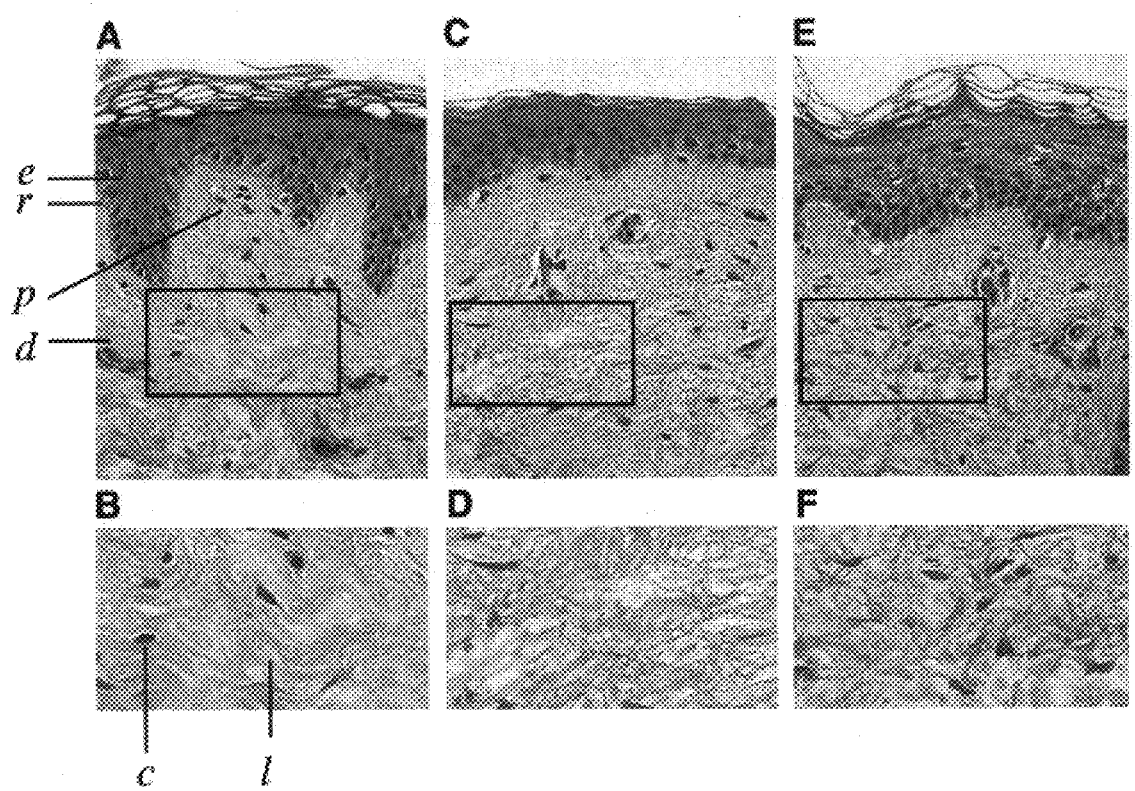
FIG. 13 shows stained cross-sections and closeups from the skin of a young individual (13A and 13B), an elderly individual (13C and 13D), and the same elderly individual (13E and 13F) after a single application of 1% retinol (occluded, left for seven days, then biopsied).

The graphic results of our novel treatments are shown in FIG. 13. FIGS. 13A and 13B are photomicrographs showing the histology appearance of sun-protected skin of a 22-year old individual, the portion in FIG. 13B being an enlarged view of the boxed area in FIG. 13A. As shown therein, the skin is composed of the epidermis E overlying the dermis D. Part of the adhesion between the epidermis and the dermis is facilitated by a large interfacial area between the epidermis and the dermis. This interface is defined by the rete pegs or ridges R that extend down from the epidermis into the dermis and by the dermal papillae P that extend up from the dermis into the epidermis. These pegs and papillae create the folds seen in the cross-section of FIG. 13A and increase the interfacial surface area between the two layers of the skin. The section at the bottom (FIG. 13B) shows a more detailed view of the dermis which contains few cells C and is mostly collagen L. As seen in this section from a younger individual, the collagen in the dermis is relatively dense and of a uniform structure.

FIGS. 13C and 13D show the histology of vehicle-treated sun-protected skin of an 86-year old individual. As seen in FIG. 13C, the epidermis is thinner in aged skin and there are essentially no rete pegs and essentially no dermal papillae. The detailed view in FIG. 13D shows that the dermis of aged skin generally has fewer cells and has collagen that is less dense and more unevenly distributed than that found in younger individuals. The thinner epidermis and decreased interfacial surface area between the epidermis and dermis tend to cause elderly people to have a higher incidence of bruising and ulcerous conditions, such as Bateman's purpura.

FIGS. 13E and 13F depict retinol-treated, sun-protected skin from the same individual from whom the biopsy shown in FIGS. 13C and 13D was taken, after 7 days having been treated as described previously (one application of retinol). The changes to the skin shown are quite remarkable and unexpected. The epidermis thickened, the interfacial surface area increased as evidence by the presence of new rete pegs and dermal papillae, and as shown in the detailed view the dermal collagen became denser and more regular in its appearance. Thus, the topical application of an effective amount of a retinoid acts to increase the thickness of the epidermis (e.g., normalize with respect to young skin), to promote the formation of rete pegs and dermal papillae, and to increase the amount, density, and regularity of the collagen in the dermis. These changes reverse the apparent histological changes seen in aged skin and help to prevent bruising, tearing, ulceration, and similar trauma in aged skin that does not occur in young skin.

Figure 14:
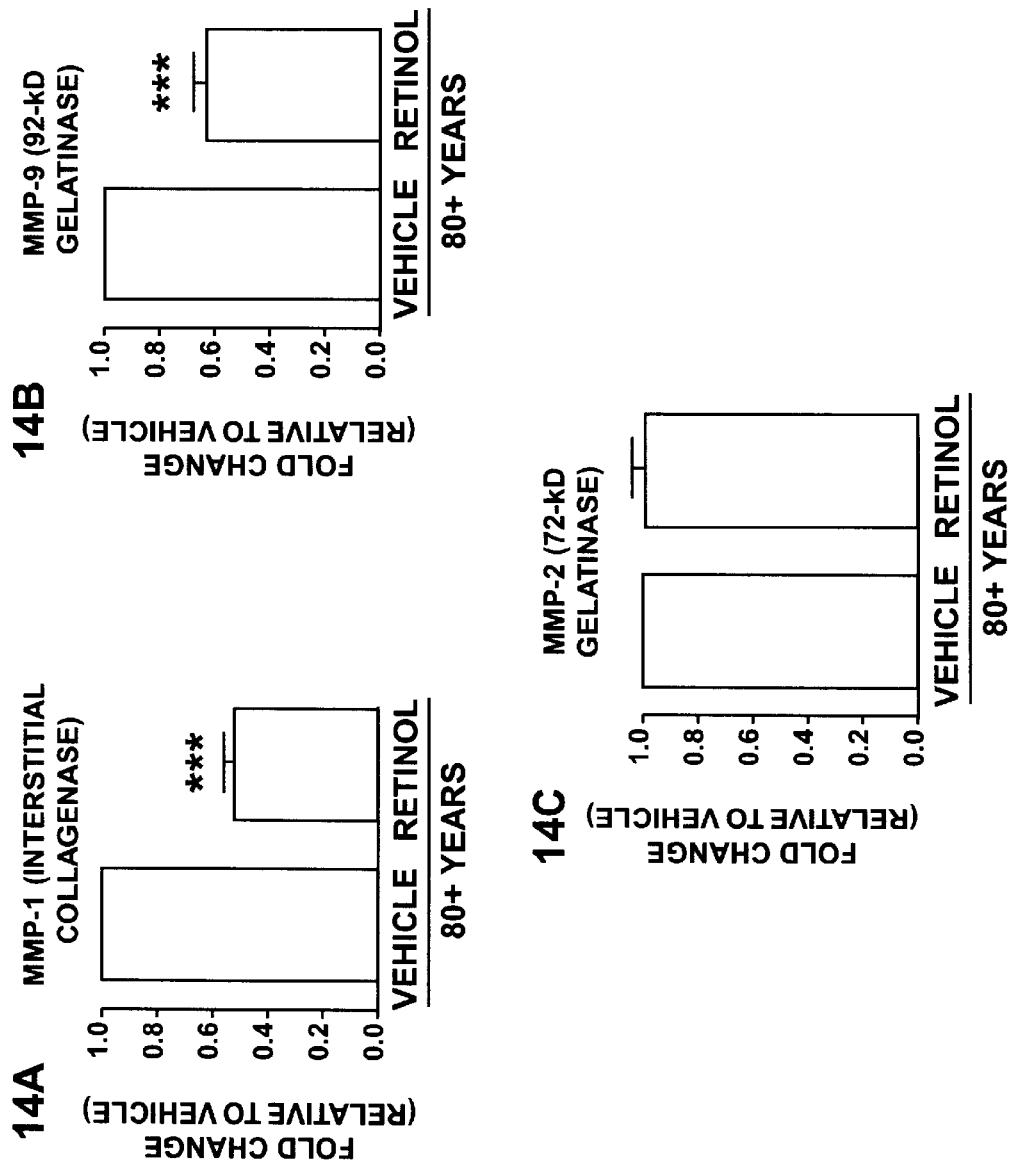
FIG. 14 depicts the effect on activities of three MMP enzymes (MMPs 1, 2, and 9; analogous to FIG. 4) after a single application of retinol to elderly skin as determined by biopsy.

We also used the biopsies from the aforementioned volunteers to determine the effect of the same retinoid treatment on the relative activity of the same collagenase enzymes studied for the results shown in FIG. 4. FIGS. 14A, 14B, and 14C depict the average MMP activity levels (for collagenase MMP-1 and gelatinases MMP-9 and MMP-2, respectively) after treatment of elderly individuals with retinol. As shown in FIG. 14, seven days after a single retinol treatment, the activities of MMP-1 and MMP-9 were both decreased (48% and 39% decreases, respectively, with $p<0.001$ for both enzymes); no significant change in the activity of MMP-2 was noted. The enzyme activities levels were significantly reduced for MMPs 1 and 9, as compared with a control treatment of the vehicle only. (In FIGS. 14A–14C, the number of subjects for each figure was 10; "*" indicates $p<0.5$ versus the 18–29 year old values, "" indicates $p<0.1$, and "*" indicates $p<0.001$.)

Figure 15:
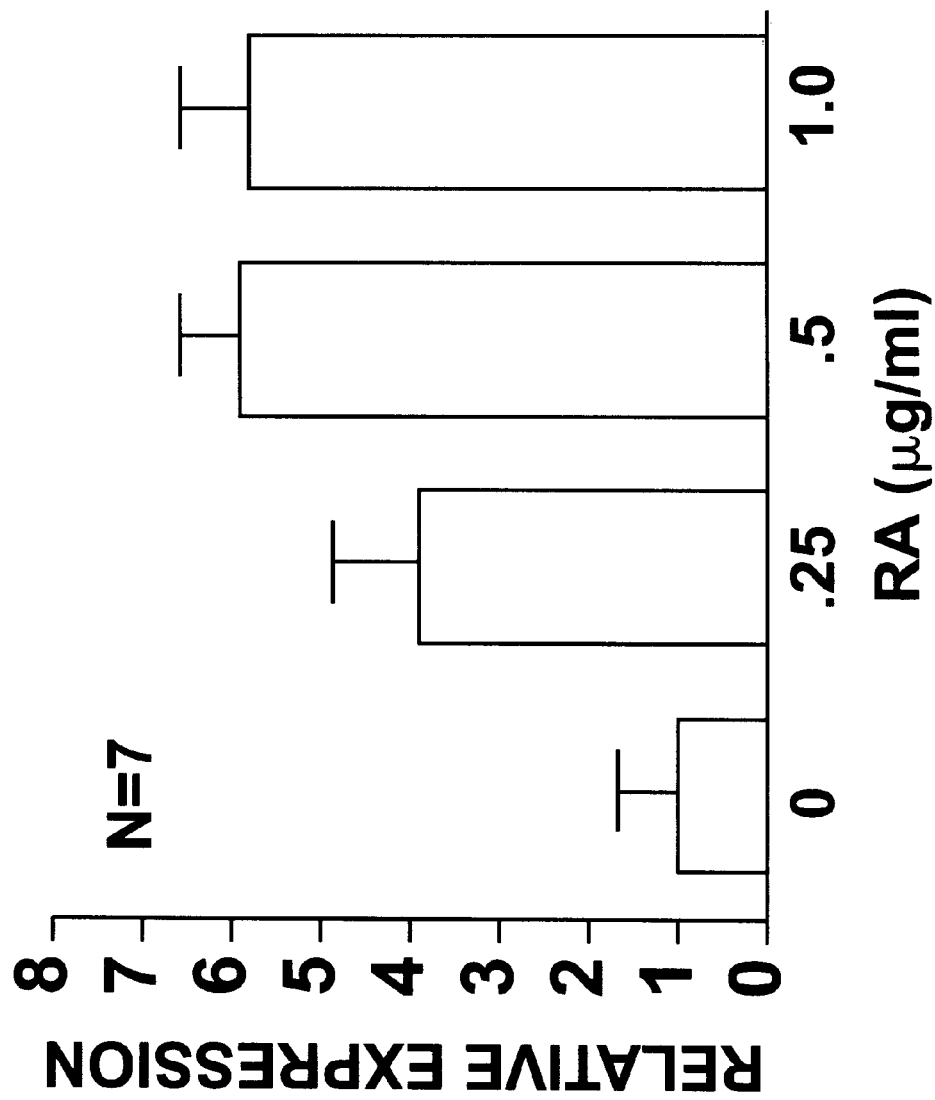
FIG. 15 depicts the retinoic acid-mediated induction of Type I collagen synthesis in cultured human skin fibroblasts.

Using the foregoing and analogous techniques, using samples from seven volunteers over 80 years old and cultured fibroblasts from biopsy samples of their unexposed (sun-protected) skin, we found that a retinoic acid concentration of 0.25 µg/ml increased the relative expression of collagen three fold from that of untreated cells, and 0.5 and 1.0 µg/ml generally increased the biosynthesis of collagen in these cultured cells five-fold from untreated cells, as shown in FIG. 15.

Figure 16:
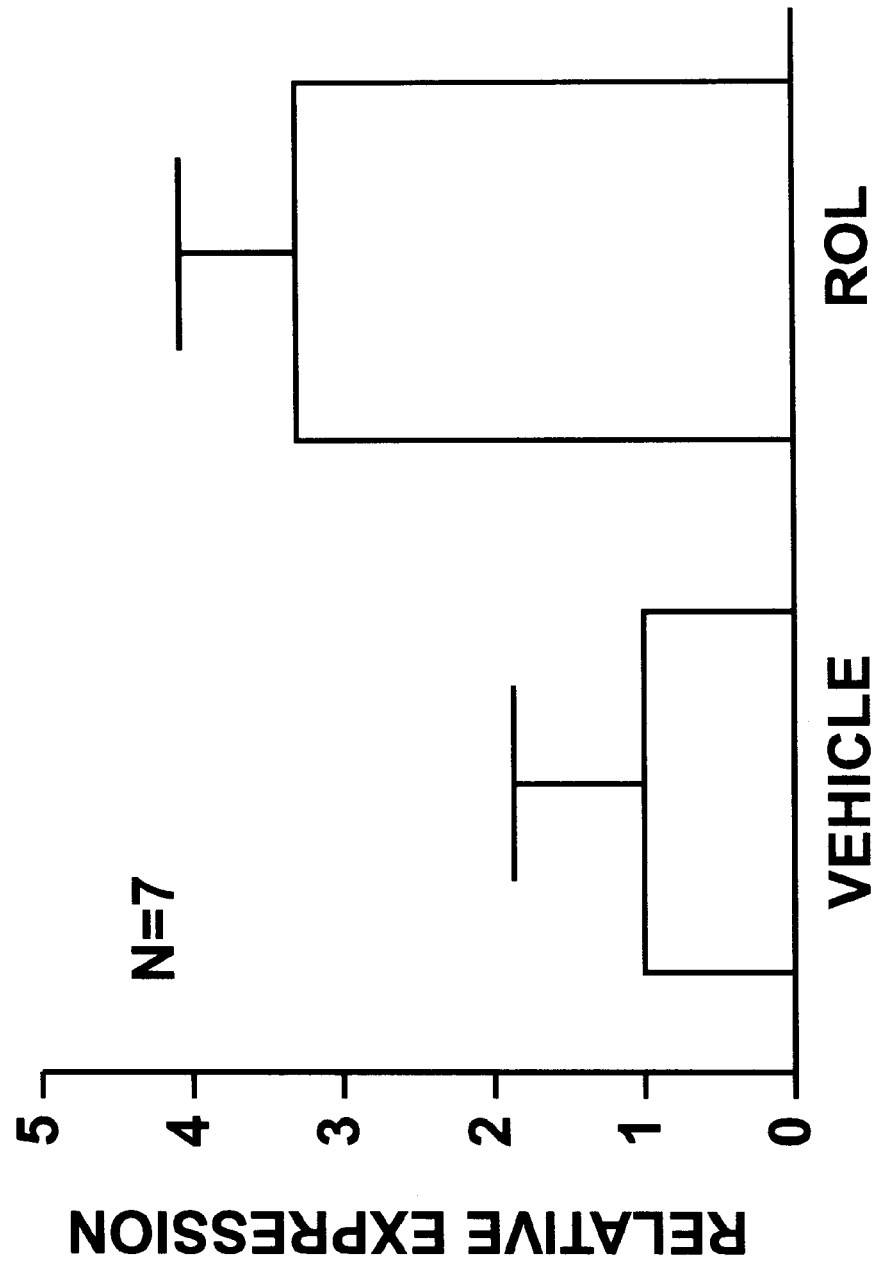
FIG. 16 depicts the in vivo induction of Type III procollagen α1(III) mRNA caused by retinol administration to elderly skin.

Seven 80+ year old individuals were treated clinically with 1% retinol cream, applied once to sun-protected skin, covered with a patch, and left undisturbed for seven days. Biopsies of these treated areas under the patch revealed that Type III procollagen mRNA had increased in these individuals' skin about 2.5 times from that of control (vehicle-treated) areas treated by the same method (single application and covered for seven days). These results are shown in FIG. 16.

Figure 17:
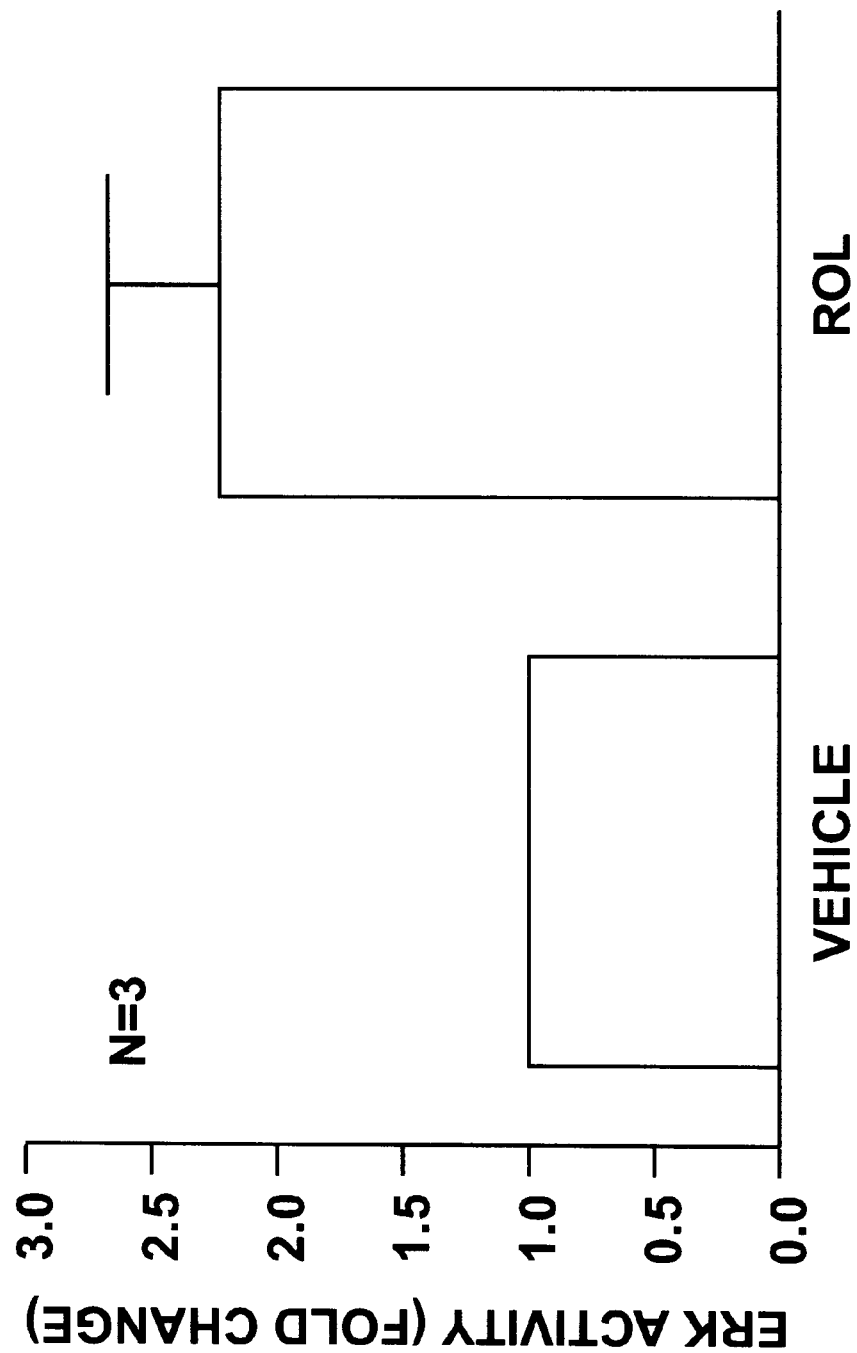
FIG. 17 depicts the in vivo induction ERK activity caused by retinol administration to elderly skin.

Using the same technique as previously described for retinoid treatment (1% retinol applied to sun-protected skin, occluded, and examined seven days later), we treated and then tested three of our 80+ year old volunteers to determine the effect of retinoid treatment on ERK activity. The results of biopsies from these individuals show that after the treatment ERK activity in vivo was more than doubled when compared with a vehicle-treated and biopsied area from the same volunteers. These results are shown in FIG. 17 (in which the control, vehicle-treated skin, was normalized to a value of one).

Additional sectioned and stained biopsies from our oldest (80+) group of volunteers after retinoid treatment are depicted in FIG. 18. As noted above, AP-1 induces MMP formation and is formed by the heterodimerization of c-Jun and c-Fos proteins. FIG. 18A shows that after one week of retinoid (retinol, "ROL") treatment, the c-Jun level in elderly skin (c-Jun being stained red) is significantly reduced (almost absent) when compared with a biopsied section from vehicle-treated skin. Thus, our invention appears to inhibit c-Jun formation and thereby inhibit the formation of AP-1 and the resulting MMPs. FIGS. 18B and 18C show that the levels of Types I and III procollagen (stained red) are enhanced in retinoid treated skin. (The apparently lower density of procollagen in the dermis in FIG. 18C is an artifact of the section made; there is clearly a higher level of staining in the retinol treated section than in the vehicle treated section.)

Accordingly, in one embodiment the invention comprises a method of rejuvenating aged skin by the application of an effective, non-toxic amount of a retinoid for an effective period of time. The effective period of time is generally daily, preferably with only one application/administration of the composition each day. Preferred treatment and maintenance regimes use an effective amount of about 0.4% retinoid, although higher doses can be used where warranted. Retinol is the preferred retinoid.

In another embodiment, the invention provides a method of inducing in vivo keratinocyte and/or fibroblast proliferation by the topical administration of an effective, non-toxic amount of a retinoid (preferably retinol or all trans retinoic acid) for an effective period of time. Again, treatment is preferably daily, once or twice, with the amount of retinoid preferably being about 0.1% to about 1.0%.

In yet another embodiment, the invention reduces and/or inhibits MMP-1 and/or MMP-9 expression in elderly skin, by the topical administration of an effective amount of a retinoid for an effective period of time; again the preferred retinoids are retinoid and all trans retinoic acid. Again, treatment is preferably daily, once or twice, with the amount of retinoid preferably being about 0.1% to about 1.0%.

As noted above, the decrease in keratinocytes and fibroblasts, and the increase in MMP expression, can be viewed as an age-related condition without resort to insults such as sun damage. This invention thus provides a prophylaxis against a detrimental change in any of these age-related parameters, as well as providing a treatment to ameliorate these detrimental etiological changes induced by aging.

In another aspect, this invention is directed to improving, or stimulating, the synthesis of Types I and III procollagen in an elderly person's skin. We have found there is a significant reduction in Types I and III procollagen synthesis in sun-protected skin of many (at least 50% of) aged individuals and that this condition can be treated by the topical application of a retinoid. Procollagen is a protein synthesized by skin fibroblast cells and then secreted into the extracellular medium, where it is converted by naturally occurring enzymes into collagen. Reduced procollagen synthesis in an elderly person's skin is manifest as a reduced presence of procollagen protein in both the upper dermis (extracellular) and in fibroblasts throughout the dermis, and can be determined (e.g.) by immunohistochemistry.

Taken together, our investigation of the control pathways shown in FIG. 1 indicate that chronological aging of skin can be caused by deactivation of ERK and/or by activation of the SAPs. In fact, we have found that both events occur in elderly skin. The results depicted in FIGS. 7–9 show that the sun-protected skin of elderly persons (which skin has generally not been exposed to the sun on a chronic basis) has reduced amounts of active ERK and a reduced amount of cyclin $D_2$, which lead to a reduction in cell growth. We have also shown in elderly skin there is a reduction in the amount of Types I and III procollagen synthesized (see FIG. 6). If there is less cell growth in the dermis, then the epidermal covering is also likely to be compromised. Our results on tests of various signalling components of the ERK pathway important for fostering growth in human skin indicate that chronological aging in human skin is characterized by a reduced activation of at least two components of the pathway that promotes cell growth. As skin ages, reduced activation of ERK and reduced production of cyclin $D_2$ lead to reduced cell growth that results, ultimately, in aged skin. Our results shown in FIGS. 15–17 prove the in vivo effectiveness of retinoid treatment in increasing the activity level of ERK and the production Types I and III procollagen.

On the other side (degradation of the dermis as opposed to creation of new dermis), the results depicted in FIGS. 4, 5, and 10 show that the unexposed skin of elderly persons has increased cJUN kinase and MMP activities. The up-regulation of the degradative MMP enzymes and the down-regulation of procollagen synthesis result in a deficiency of collagen, causing skin aging and impaired repair of aged skin. An increase in the pathway activity that causes an increased rate of breakdown of the skin (such as though MMP-mediated degradation of the dermal matrix and inhibition of procollagen synthesis) concomitant with a decrease in the pathway activity that promotes cell growth (such as a decrease in ERK activity) both contribute to chronoaging of human skin. Our methods for preventing and rejuvenating chronologically-aged skin, while tested on unexposed, sun-protected skin, often with occlusion of the site treated, are applicable to treating chronoaging of the skin over the entire body, including the face and hands. Taken with the teachings of the aforementioned patent and provisional applications directed to photoaging, daily application of a retinoid to the skin will ameliorate the effects of natural aging as well as the sun's exacerbating effects on natural aging of the skin.

Thus, while not desirous of being constrained to a particular theory of function, we believe that the results shown, for example, in FIGS. 13E and 13F are due, at least in part, to some combination of improved ERK activation, decreased amounts of c-Jun, and increased amounts of Types I and/or III procollagen. Using the same technique described for retinoid treatment (1% retinol applied to sun-protected skin, occluded, and examined seven days later), we tested three of our 80+ year old volunteers. The results of biopsies from these individuals show that after the treatment ERK activity in vivo was more than doubled, as shown in FIG. 13 (in which the control, vehicle-treated skin, was normalized to a value of one).

Retinoids are one class of MMP inhibitors. The inhibitors of MMPs can act directly on the MMPs and/or on the transcription factors AP-1 and NF-κB by which MMPs are produced naturally. Aspirin and E5510 (described by Fujimori, T., et at., Jpn J Pharmacol (1991) 55(1):81–91) inhibit NF-κB activation. Retinoids such as those disclosed in U.S. Pat. No. 4,877,805 and the dissociating retinoids that are specific for AP-1 antagonism (such as those described by Fanjul, et al. in Nature (1994) 372:104–110), glucocorticoids, and Vitamin $D_3$ target AP-1. Compounds for enhancing the therapeutic effect of Vitamin $D_3$ are described in copending application Ser. No. 08/832,865 (J. Voorhees et al., "Method for Assessing 1,25(OH)$_2$D$_3$ Activity in Skin and for Enhancing the Therapeutic Use of 1,25(OH)$_2$D$_3$"), filed Apr. 4, 1997, the disclosure of which is incorporated herein by reference. Other retinoids, besides retinol, include natural and synthetic analogs of vitamin A (retinol), vitamin A aldehyde (retinal), vitamin A acid (retinoic acid (RA)), including all-trans, 9-cis, and 13-cis retinoic acid), etretinate, and others as described in EP-A2-0 379367, U.S. Pat. Nos. 4,887,805, and 4,888,342 (the disclosures of which are all incorporated herein by reference). Various synthetic retinoids and compounds having retinoid activity are expected to be useful in this invention, to the extent that they exhibit retinoid activity in vivo, and such are described in various patents assigned on their face to Allergan Inc., such as in the following U.S. Pat. Nos.: 5,514,825; 5,698,700; 5,696,162; 5,688,957; 5,677,451; 5,677,323; 5,677,320; 5,675,033; 5,675,024; 5,672,710; 5,688,175; 5,663,367; 5,663,357; 5,663,347; 5,648,514; 5,648,503; 5,618,943; 5,618,931; 5,618,836; 5,605,915; 5,602,130. Still other compounds described as having retinoid activity are described in other U.S. Pat. Nos.: 5,648,563; 5,648,385; 5,618,839; 5,559,248; 5,616,712; 5,616,597; 5,602,135; 5,599,819; 5,556,996; 5,534,516; 5,516,904; 5,498,755; 5,470,999; 5,468,879; 5,455,265; 5,451,605; 5,343,173; 5,426,118; 5,414,007; 5,407,937; 5,399,586; 5,399,561; 5,391,753; and the like, the disclosures of all of the foregoing and following patents and literature references hereby incorporated herein by reference.

MMPs are also inhibited by BB2284 (described by Gearing, A. J. H. et al., Nature (1994) 370:555–557), GI129471 (described by McGeehan G. M., et al., Nature (1994) 370:558–561), and TIMPs (tissue inhibitors of metalloproteinases, which inhibit vertebrate collagenases and other metalloproteinases, including gelatinase and stromelysin). Still other compounds useful for the present invention include hydroxamate and hydroxy-urea derivatives, such as Galardin, Batimastat, and Marimastat, and those disclosed in EP-A1-0 558635 and EP-A1-0 558648 (disclosed therein as useful for inhibiting MMPs in the treatment of, among other etiologies, skin ulcers, skin cancer, and epidermolysis bullosa). Retinoids have been reported by Goldsmith, L. A. (*Physiology, Biochemistry, and Molecular Biology of the Skin,* 2nd. Ed. (New York: Oxford Univ. Press, 1991), Chpt. 17) to cause an increase in steady state levels of TIMP mRNA that would suggest transcriptional control; although, based on our discoveries, we have found this is not true in human skin in vivo. Still other inhibitors of MMPs that can be applied topically and are useful in practicing the claimed invention include the tetracyclines and derivatives thereof, such as minocycline, roliteracycline, chlortetracycline, methacycline, oxytetracycline, doxycycline, demeclocycline, and the various salts thereof. Because of possible allergic or sensitization reactions, the topical administration of tetracyclines should be monitored carefully for such untoward reactions. Other MMP inhibitors include genistein and quercetin (as described in U.S. Pat. Nos. 5,637,703, 5,665,367, and FR-A-2,671,724, the disclosures of which are incorporated herein by reference) and related compounds, as well as other antioxidants such as NAC (N-acetyl cysteine), green tea extract, and others.

The effective amount of the active ingredient applied to the skin is preferably in the range of about 0.001–5 wt. %, more preferably about 0.01–2 wt. %, still more preferably 0.1–1 wt. % of the total weight of the composition. Compositions are formulated to provide preferably about 5 $\mu$g/cm$^2$ skin when applied. For example, a preferred composition for use in this invention is Retin-A® retinoic acid gel and cream (available from Ortho Pharmaceuticals for the treatment of acne vulgaris), in strengths of from 0.01% to 0.1%; the vehicle preferably includes, depending upon the particular formulation, at least one of butylated hydroxytoluene, alcohol (denatured with t-butyl alcohol and brucine sulfate), stearic acid, isopropyl myristate, polyoxyl 40 stearate, stearyl alcohol, and the like, and compatible mixtures thereof We tested fifteen subjects in two age groups, young subjects (19–29 years old) and elderly subjects (over 80 years old) to determine the degree of activation of the SAP kinase in each group; SAP kinase activity is measured by the phosphorylation of c-Jun. FIG. 10 shows that in vivo samples of unexposed skin from the young subjects had about 25% of the relative cJUN kinase activity than did unexposed skin from elderly subjects. From these results, one would then expect correspondingly elevated levels of AP-1 and MMPs in the skin of elderly.

It has been found unexpectedly that topical treatment of elderly, chronoaged skin with a retinoid results in a restitution of intracellular procollagen protein levels similar to those observed in young individuals (such as those aged 40 and younger). In particular, we have found that a single application of 1% retinol to chronologically-aged skin, covered with an air-permeable adhesive bandage, and examined seven days later, resulted in procollagen protein levels comparable to those found in sun-protected skin of significantly younger individuals (e.g., under age 40). It would be more preferable for elderly persons to apply the retinoid once or twice daily to maintain a therapeutic regimen, although the agent could be applied on a less frequent but preferably regular basis (e.g., every other day, or once weekly). It may also be desirable for the skin to be occluded from environmental insults, particularly sources of UV light, detergents and other harsh chemicals, and the like. Accordingly, it would be beneficial to add to the retinoid composition a UV sunscreen, an antioxidant, and the like.

The stimulation of procollagen production is an important factor in maintaining the integrity of chronologically-aged skin. Aged skin is thin and fragile due, in part, to reduced collagen content and reduced collagen fiber organization. Stimulation of procollagen synthesis by retinoids, and its subsequent conversion to collagen, would be expected to reduce the fragility, increase the thickness, and improve the appearance of aged skin. Accordingly, this invention provides methods for increasing procollagen concentrations, both intra- and extracellularly, and so also to improving collagen concentrations, all in chronologically-aged skin. Additionally, as shown herein, MMP levels are increased in elderly skin compared to those found in the skin of younger persons. Improved production of procollagen would be frustrated if the resulting collagen were degraded in the skin, and so treatment of elderly skin with both a retinoid and an MMP inhibitor is important for achieving the desired benefits of improved procollagen biosynthesis. In fact, we have found in skin not having a reduced level of collagen, treatment with a retinoid does not elevate the collagen levels above normal; hence, our invention shows that application of a retinoid can restore collagen levels to their desired baseline value. Thus, our inventive treatment with a the MMP activities that cause epidermal thinning.

Although retinol is the preferred compound for topical administration, effective derivatives of retinol that would be expected to be useful for practicing this invention include retinal, retinoic acid (including all trans, 9-cis, and 13-cis isomers) and derivatives thereof (such as 7,8-didehydroretinoic acid), and others as described by Kligman et al., referred to above, the disclosure of which is incorporated herein by reference, including cosmetically acceptable salts, esters, reverse esters, and ethers thereof, conjugates thereof, and mixtures thereof.

The compositions described herein formulated on a commercial basis can include various conventional colorants, fragrances, thickeners (such as xanthan gum), preservatives, humectants, emollients, demulcents, surfactants, dispersants, penetration enhancers, and the like can be added to provide additional benefits and improve the feel and/or appearance of the topical preparation. Likewise, the composition can be formulated as a cream, lotion, ointment, soap or body wash, shampoo, or a mask.

The foregoing description and following methods are meant to be illustrative of the invention and not limiting. Various changes, modifications, and additions may become apparent to the skilled artisan upon a perusal of this specification, and such are meant to be within the scope and spirit of the invention as defined by the claims.

Methods Used in the Examples

The references noted in this section are incorporated herein by reference.

Histology and morphometry. Replicate 4-mm punch biopsies were obtained from buttock skin of each individual. Formalin-fixed tissue pieces were sectioned, stained with hematoxylin and eosin, randomized and blinded. The sections were examined using an Olympus BX40 microscope in conjunction with a Sony DCX-151 high-resolution camera. Blocked areas 200 $\mu$m on a side were isolated using NIH Imager software and epidermal height was assessed at four sites (25 $\mu$m apart) in each of two such areas. The same two blocked areas were used for epithelial cell counts. The number of interstitial cell nuclei (i.e., nuclei below the dermo-epidermal juncture, not associated with capillaries) over the entire histological section was determined as a measure of dermal cellularity. The same blinded sections were scored for connective tissue fiber spacing, thickness, degree of disorganization and depth of disorganization, using a scale of 1–9 for each parameter.

Preparation of skin supernatants for biochemical analysis. Skin samples were ground by mortar and pestle under liquid nitrogen, and homogenized in a Dounce tissue grinder in buffer containing 10 mM Hepes, 1 mM EDTA, 5 mM EGTA, 10 mM $MgCl_2$, 50 mM glycerophosphate, 5 mM $NaVO_4$, 2 mM DTT, 0.5 mM PMSF, 10 $\mu$g/ml aprotinin, 10 $\mu$g/ml leupeptin, and 10 $\mu$g/ml pepstatin, and 0.5% NP-40. Homogenates were centrifuged at 14,000 g for 15 min., and supernatants were collected and used for biochemical determinations as described herein.

Ex vivo cell growth. Biopsies were minced into small fragments (approximately 15 fragments per tissue piece) and the tissue fragments transferred to plastic cell culture flasks. Culture medium consisted of Dulbecco's Modified Minimal Essential Medium of Eagle with Earle's salts, non-essential amino acids and 10% fetal bovine serum. Tissue fragments were incubated at 37° C. and 5% $CO_2$/95% air for up to one month. Each fragment was scored for whether keratinocytes and/or fibroblasts grew out of the tissue and from this, the percentage of fragments from which keratinocytes and fibroblasts were isolated was determined according to the method of Varani, J., et al., *J Clin. Invest.*, 96, 1747–1756 (1994).

Matrix metalloproteinase assays. Tissue pieces were frozen in liquid nitrogen immediately after biopsy, homogenized in 20 mM Tris HCl (pH 7.6) plus 5 mM $CaCl_2$, and centrifuged at 3000×g for 10 minutes to remove particulates. Ability to release soluble radioactive fragments from 3H-labeled fibrillar Type I collagen (described by Fisher, G. J., et al., *Nature*, 379, 335–339 (1996) and Hu, C-L, et al., *Analytic. Biochem*, 88, 638–643 (1978)) was used as a measure of collagenolytic activity. Tissue extracts were incubated for 3 hours with 1 mM aminophenyl mercuric acetate (APMA) to convert the inactive form of the matrix metalloproteinase into an active form. Subsequently, 0.2 $\mu$Ci of collagen substrate (NEN-DuPont, Boston, Mass.) was incubated for 24 hours with 50 $\mu$l of tissue extract. At the end of the 24-hour incubation period, the samples were centrifuged at 12,000×g for 10 minutes to pellet the intact protein. Radioactivity remaining in the supernatant fluid was then measured and from this, the percentage of substrate hydrolzyed was determined.

Gelatin zymography (Varani et al., op. cit.) was used to assess MMP-2 (72-kD gelatinase; gelatinase A) and MMP9 (92-kD gelatinase; gelatinase B) activity. Tissue extracts were electrophoresed in an 8.5% SDS-polyacrylamide gel containing 1 mg/ml of gelatin. After electrophoresis, the SDS was removed by three sequential washes in 1% Triton X-100. The first two washes were for 20 minutes each and the last was overnight. Quantitation of hydrolysis zone width was done by laser densitometry.

ERK phosphorylation and activity assays. ERK1 and ERK2 in skin supernatants were immunoprecipitated with antibodies from Santa Cruz Biotechnology Inc. and assayed for enzymatic activity using myelin basic protein as substrate, as described by J. D. Weber et al. ("Sustained activation of extracellular-signal regulated kinase I (ERK1) is required for the continued expression of cyclin D1 in G1 phase," *Biochem. J.*, 326:61–68 (1997)). Total and phosphorylated ERK1 and ERK2 in supernatants were determined by Western analysis, using antibodies from New England Biolabs Inc. (Beverly, Mass.)

c-Jun kinase activity assay. c-Jun activity in skin supernatants was determined by solid phase kinase assays (as described, e.g., by M. Hibi et al., "Identification of an oncoprotein and UV-responsive protein kinase that binds and potentiates the c-Jun activation domain," *Genes Dev.*, 7:2135–2148 (1993)).

Northern analysis of RNA. Total RNA (e.g., for c-Jun, procollagen $\alpha 1$(III)) was isolated from skin samples by guanidinium hydrochloride lysis and ultracentrifugation (as described by G. J. Fisher et al., "Cellular, immunologic and biochemical characterization of topical retinoic acid-treated human skin," *J Investig. Dermatol*, 96:699–707 (1991)). Northern analysis of total RNA (40 $\mu$g/lane) with randomly primed $^{32}$P labelled cDNA probes for the particular mRNA to be determined were performed as described by G. J. Fisher et al. (in "All trains retinoic acid induces cellular retinol-binding protein in human skin in vivo," *J Investig. Dermatol*, 105:80–86 (1995)). Type III procollagen mRNA was determined using reverse transcriptase polymerase chain reaction.

Western analysis of proteins. Jun proteins, cyclin $D_2$ (both antibodies from Santa Cruz Biotechnology Inc.), and phosphorylated c-Jun (antibody from New England Biolabs Inc.) were detected in nuclear extracts from human skin by Western analysis as described by G. J. Fisher et al. (in "Immunological identification and functional quantitation of retinoic acid and retinoid X receptor proteins in human skin," *J Biol. Chem.*, 269:20629–20635 (1994)).

Immunoreactive proteins were visualized by enhanced chemiluminescence detection and quantified by laser densitometry, or by enhanced chemifluorescence detection and quantified by a Storm imager (Molecular Dynamics, Palo Alto, Calif.).

What is claimed is:

1. A method of reducing the natural, chronological, age-related elevation of collagen-degrading MMP enzymes present in chronologically-aged skin, comprising the topical application to said chronologically-aged skin of an effective, non-toxic amount of at least one active non-retinoid ingredient that inhibits MMPs.

2. The method of claim 1, further comprising reducing the natural, chronological, age-related reduction in collagen biosynthesis present in chronologically-aged skin by stimulating the formation of new collagen by the co-administration of a retinoid in an amount effective to promote procollagen biosynthesis.

3. The method of claim 2, wherein the retinoid is selected from retinol, retinal, retinoic acid, a retinoic acid salt, a derivative or analog thereof, or a mixture thereof.

4. The method of claim 3, wherein the retinoid is retinol or retinoic acid.

5. The method of claim 3, wherein the skin is sun-protected skin.

6. The method of claim 1, wherein the MMP inhibitor is selected from aspirin, E5510, glucocorticoids, Vitamin $D_3$, GI12947, TIMPs, hydroxamates and hydroxy-urea derivatives, and tetracyclines and derivatives thereof, and the various salts thereof.

7. A method of delaying the onset and reducing the natural, chronological, age-related (I) elevation of collagen-degrading MMP enzymes and (ii) reduction in collagen biosynthesis present in such chronologically-aged skin present after about 80 years of age, comprising providing a topically administrable, non-toxic amount of a retinoid in a cosmetically suitable vehicle and applying said retinoid to the skin of a person less than about 80 years old at least once weekly in an amount effective to delay said onset of and to reduce said chronological, age-related decrease in procollagen synthesis and increase in collagen degradationing MMP enzymes present in said chronologically-aged skin.

8. The method of claim 7, wherein the skin is sun-protected skin.

9. The method of claim 7, wherein the retinoid is selected from retinol, retinal, retinoic acid, a retinoic acid salt, a derivative or analog thereof, or a mixture thereof.

10. The method of claim 9, wherein the retinoid is retinol.

11. The method of claim 7, wherein the retinoid is applied daily.

12. The method of claim 7, further comprising administering a non-retinoid MMP inhibitor compatible with said retinoid and together therewith in a cosmetically suitable vehicle and applying said retinoid and said non-retinoid MMP inhibitor in combination to the skin.

13. The method of claim 12, wherein the combination is administered daily.

14. A method for increasing the production of procollagen and the amount of collagen present in chronologically-aged skin, comprising the steps of providing a topically administrable, non-toxic retinoid and a non-toxic non-retinoid MMP inhibitor and co-administering said retinoid and said non-retinoid MMP inhibitor to the skin in an amount effective to bring the amount of collagen back to levels normally found in skin and to decrease the degradation of collagen by MMPs.

15. The method of claim 14, wherein the retinoid is retinol.

16. The method of claim 14, wherein the retinoid is applied on a regular basis.

17. The method of claim 16, wherein the retinoid is applied daily.

18. The method of claim 14, wherein the MMP inhibitor is selected from aspirin, E5510, glucocorticoids, Vitamin $D_3$, GI12947, TIMPs, hydroxamates and hydroxy-urea derivatives, and tetracyclines and derivatives thereof, and the various salts thereof, and compatible mixtures thereof.

19. The method of claim 14, wherein said retinoid and said MMP inhibitor are present in a single, topically administered formulation.

20. The method of claim 14, wherein the chronologically-aged skin is sun-protected skin.

21. The method of claim 1, wherein the MMP inhibitor is selected from the group consisting of genistein, galardin, batimastat, marimastat, N-acetyl cysteine, and green tea extract.

22. The method of claim 21, wherein more than one MMP inhibitors is topically applied.

23. The method of claim 21, wherein the MMP inhibitor is genistein.

24. The method of claim 21, further comprising stimulating the formation of new collagen by the co-administration of a retinoid in an amount effective to promote procollagen biosynthesis.

25. The method of the retinoid is retinol.

26. The method of claim 24, Wherein the retinoid is retinal.

27. The method of claim 24, wherein the retinoid is retinoic acid.

28. The method of claim 24, wherein the retinoid is a retinoic acid salt.

29. The method of claim 21, used in alternation with a retinoid.

30. The method of claim 29, wherein the retinoid is retinol.

31. The method of claim 29, wherein the retinoid is retinal.

32. The method of claim 29, wherein the retinoid is retinoic acid.

33. The method of claim 29, wherein the retinoid is retinoic acid salt.

34. The method of claim 21, further comprising a pharmaceutically acceptable carrier.

35. The method of claim 21, wherein the MMP inhibitor is applied weekly.

36. The method of claim 21, wherein the MMP inhibitor is applied daily.

37. The method of claim 24, wherein the combination is applied weekly.

38. The method of claim 24, wherein the combination is applied daily.

* * * * *